US012560603B2

(12) United States Patent
Erickson et al.

(10) Patent No.: US 12,560,603 B2
(45) Date of Patent: Feb. 24, 2026

(54) SELF-CONTAINED APPARATUS AND SYSTEM FOR DETECTING MICROORGANISMS

(71) Applicant: Laboratory Corporation of America Holdings, Burlington, NC (US)

(72) Inventors: Stephen E. Erickson, White Bear Township, MN (US); John Paulson, Burlington, NC (US); Minh Mindy Bao Nguyen, Shoreview, MN (US); Jessica Stach, Burlington, NC (US); Jose S. Gil, Winnetka, CA (US); Dwight L. Anderson, Minneapolis, MN (US); Wendy Hahn, Hugo, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 915 days.

(21) Appl. No.: 16/709,567

(22) Filed: Dec. 10, 2019

(65) Prior Publication Data

US 2020/0182869 A1    Jun. 11, 2020

Related U.S. Application Data

(60) Provisional application No. 62/798,980, filed on Jan. 30, 2019, provisional application No. 62/777,473, filed on Dec. 10, 2018.

(51) Int. Cl.
| | |
|---|---|
| *C12Q 1/70* | (2006.01) |
| *B01L 3/00* | (2006.01) |
| *G01N 33/535* | (2006.01) |
| *G01N 33/569* | (2006.01) |

(52) U.S. Cl.
CPC ...... *G01N 33/56911* (2013.01); *B01L 3/5029* (2013.01); *C12Q 1/70* (2013.01); *G01N 33/535* (2013.01); *C12N 2795/00031* (2013.01); *C12Y 113/12* (2013.01)

(58) Field of Classification Search
None
See application file for complete search history.

(56) References Cited

U.S. PATENT DOCUMENTS

| | | |
|---|---|---|
| 2006/0210968 A1 | 9/2006 | Goodridge |
| 2014/0272928 A1* | 9/2014 | Rey ..................... C12Q 1/6897 435/5 |

| | | |
|---|---|---|
| 2015/0218613 A1 | 8/2015 | De Forest et al. |
| 2019/0276868 A1 | 9/2019 | Erickson et al. |
| 2020/0182869 A1 | 6/2020 | Erickson et al. |

FOREIGN PATENT DOCUMENTS

| | | |
|---|---|---|
| CN | 106461535 A | 2/2017 |
| EP | 3762724 A1 | 1/2021 |
| EP | 3894859 A1 | 10/2021 |
| JP | 2016519566 A | 7/2016 |
| JP | 2017513496 A | 6/2017 |
| WO | 2015164746 A1 | 10/2015 |
| WO | 2019173838 A1 | 9/2019 |
| WO | 2020123542 A1 | 6/2020 |

OTHER PUBLICATIONS

Hazbon et al., Journal of Clinical Microbiology, Oct. 2003, 41(10):4865-4869. (Year: 2003).*
Banaiee et al., Journal of Clinical Microbiology, Nov. 2001, 39(11):3883-3888. (Year: 2001).*
Schofield et al., Bacteriophage, 2012, 2(2):105-283. (Year: 2012).*
Smartt et al., Anal Bioanal Chem, 2011, 400:991-1007. (Year: 2011).*
Canadian Application No. 3,120,328, Office Action mailed on Mar. 21, 2022, 3 pages.
Carriere et al., Conditionally Replicating Luciferase Reporter Phages: Improved Sensitivity for Rapid Detection and Assessment of Drug Susceptibility of Mycobacterium Tuberculosis, Journal of Clinical Microbiology, vol. 35, No. 12, Dec. 1, 1997, pp. 3232-3239.
Chinese Application No. 201980081153.4, Office Action mailed on May 20, 2023, 20 pages. (8 pages of Original Document and 12 pages of English Translation).
Chinese Application No. 201980081153.4, Office Action mailed on Jan. 22, 2024, 17 pages.
European Application No. 19832253.9, Intention to Grant mailed on Mar. 5, 2024, 9 pages.
European Application No. 19832253.9, Office Action mailed on Nov. 29, 2022, 4 pages.
European Application No. 19832253.9, Office Action mailed on Aug. 18, 2023, 6 pages.
Japanese Application No. 2021-532880, Office Action mailed on Oct. 6, 2023, 11 pages. (4 pages of Original Document and 7 pages of English Translation).
International Application No. PCT/US2019/065528, International Preliminary Report on Patentability mailed on Jun. 24, 2021, 7 pages.

(Continued)

*Primary Examiner* — Nicole Kinsey White
(74) *Attorney, Agent, or Firm* — Kilpatrick Townsend & Stockton LLP

(57) ABSTRACT

Disclosed herein are devices, methods, and systems for rapid detection of microorganisms using a recombinant bacteriophage. The specificity of recombinant bacteriophages for binding microorganisms allows targeted and highly specific detection of a microorganism of interest.

17 Claims, 17 Drawing Sheets

(56)             References Cited

OTHER PUBLICATIONS

International Application No. PCT/US2019/065528, International Search Report and Written Opinion mailed on Mar. 10, 2020, 11 pages.

Smartt et al., Bacteriophage Reporter Technology for Sensing and Detecting Microbial Targets, Analytical and Bioanalytical Chemistry, vol. 400, No. 4, May 2011, pp. 991-1007.

Office Action issued in Canadian Application No. 3,120,328 issued Apr. 8, 2024, 4 pages.

Office Action issued in Japan Application No. 2021-532880, issued Jul. 11, 2024, 10 pages.

Office Action issued in Chinese Patent Application No. 201980081153. 4, issued Jul. 22, 2024, 13 pages.

Notice of Final Rejection issued in JP 2021-532883 dated Jun. 11, 2024, 10 pages.

Office Action issued in CN 201980081153.4 dated Jul. 22, 2024, 13 pages.

Extended European Search Report issued in EP 24194423.0 dated Dec. 20, 2024, 9 pages.

Office Action issued in CA 3, 120,328 dated May 8, 2025, 3 pages.

* cited by examiner

Table 1

Single Snap Tubes 10 ul of 1:4 dilution substrate 4 hour infection

| Sample # | Expected Cell Count | Hygiena Handheld Signal (1.2mL) | | | GloMax 20/20 Signal (1 mL) | | | | GloMax signal (150 ul of 1.2 ml) | | | | GloMax Signal x 8 (1.2mL equivalent) |
|---|---|---|---|---|---|---|---|---|---|---|---|---|---|
| | | Run 1 | Run 2 | Avg | Run 1 | Run 2 | Avg | S/B | Run 1 | Run 2 | Avg | S/B | RLU |
| neg control | 0 | 2 | 1 | 1.5 | 75111* | 6881 | 6881 | 1.0 | 608 | 582 | 595 | 1.0 | 4760 |
| 1 | 10 | 3 | 2 | 2.5 | 7567 | 7785 | 7676.5 | 1.1 | 654 | 657 | 656 | 1.1 | 5244 |
| 2 | 100 | 2 | 2 | 2 | 7887 | 8015 | 7951 | 1.2 | 610 | 668 | 639 | 1.1 | 5112 |
| 3 | 1,000 | 4 | 3 | 3.5 | 11281 | 10875 | 11078 | 1.6 | 924 | 960 | 942 | 1.6 | 7536 |
| 4 | 2,000 | 4 | 4 | 4 | 13885 | 13715 | 13800 | 2.0 | 1370 | 1365 | 1368 | 2.3 | 10940 |
| 5 | 4,000 | 5 | 5 | 5 | 19316 | 19107 | 19211.5 | 2.8 | 1741 | 1704 | 1723 | 2.9 | 13780 |
| 6 | 6,000 | 6 | 5 | 5.5 | 27277 | 27220 | 27248.5 | 4.0 | 2697 | 2715 | 2706 | 4.5 | 21648 |
| 7 | 8,000 | 6 | 6 | 6 | 30574 | 30183 | 30376.5 | 4.4 | 2846 | 2729 | 2788 | 4.7 | 22300 |
| 8 | 10,000 | 7 | 9 | 8 | 46911 | 46799 | 46855 | 6.8 | 4819 | 4850 | 4835 | 8.1 | 38676 |
| 9 | 25,000 | 12 | 12 | 12 | 85397 | 84315 | 84856 | 12.3 | 7675 | 7644 | 7660 | 12.9 | 61276 |
| 10 | 50,000 | 20 | 20 | 20 | 179065 | 178759 | 178912 | 26.0 | 19181 | 18876 | 19029 | 32.0 | 152228 |
| 11 | 100,000 | 38 | 39 | 38.5 | 387890 | 385559 | 386724.5 | 56.2 | 39577 | 38611 | 39094 | 65.7 | 312752 |
| 12 | 1,000,000 | 371 | 367 | 369 | 4535417 | 4504688 | 4520052.5 | 656.9 | 455802 | 448071 | 451937 | 759.5 | 3615492 |

Table 2

O/N incubation 2 hour infection

| Sample # | Spike before O/N incubation | Hygiena Handheld Signal (1.2mL) | | | GloMax 20/20 Signal (1 mL) | | | | GloMax signal (150 ul of 1.2 ml) | | | | GloMax Signal x 8 (1.2mL equivalent) |
|---|---|---|---|---|---|---|---|---|---|---|---|---|---|
| | | Run 1 | Run 2 | Avg | Run 1 | Run 2 | Avg | S/B | Run 1 | Run 2 | Avg | S/B | RLU |
| neg control | 0 | 9499 | 9453 | 9476 | 8103 | 8172 | 8137.5 | 1.0 | 630 | 639 | 635 | 1.0 | 5076 |
| 1 | 10 | 8922 | 8875 | 8898.5 | 1264787968 | 1263354496 | 1264071232 | 155339.0 | 120782912 | 120271104 | 120527008 | 189955.9 | 964216064 |
| 2 | 10 | | | | 607686016 | 594884942 | 601285504 | 73890.7 | 60891648 | 60485704 | 60688675 | 95648.0 | 485509408 |

FIG. 2

Table 3

Uninoculated Sample (#24)

| Turkey Samples Enriched Overnight | Hygiena | | | 20/20 | | | | 96 plate | | | |
|---|---|---|---|---|---|---|---|---|---|---|---|
| | Run #1 | Run#2 | Avg. | Run #1 | Run#2 | Avg. | S/B* | Run #1 | Run#2 | Avg. | S/B** |
| No enrichment, ½ hour infection Swab 1 | 0 | 0 | 0.25 | 885 | 904 | 951.5 | 1.0 | 80 | 62 | 84.25 | 0.8 |
| No enrichment, ½ hour infection Swab 2 | 1 | 0 | | 975 | 1042 | | | 101 | 94 | | |
| No enrichment, 2 hour infection Swab 1 | 0 | 0 | 0 | 335 | 312 | 351 | 0.4 | 56 | 35 | 65.25 | 0.7 |
| No enrichment, 2 hour infection Swab 2 | 0 | 0 | | 419 | 338 | | | 90 | 80 | | |
| 1 hr enrichment, ½ hour infection Swab 1 | 0 | 0 | 0 | 937 | 910 | 939.5 | 0.9 | 79 | 91 | 86.75 | 0.9 |
| 1hr enrichment, ½ hour infection Swab 2 | 0 | 0 | | 928 | 983 | | | 86 | 91 | | |

Table 4

Inoculated Sample (#26)

| Turkey Samples Enriched Overnight | Hygiena | | | 20/20 | | | | 96 plate | | | |
|---|---|---|---|---|---|---|---|---|---|---|---|
| | Run #1 | Run#2 | Avg. | Run #1 | Run#2 | Avg. | S/B* | Run #1 | Run#2 | Avg. | S/B** |
| No enrichment, ½ hour infection Swab 1 | 249 | 252 | 231.3 | 5612047 | 5617007 | 5185788 | 5185.8 | 488697 | 495305 | 452987 | 4529.9 |
| No enrichment, ½ hour infection Swab 2 | 209 | 215 | | 4758881 | 4755216 | | | 410597 | 417349 | | |
| No enrichment, 2 hour infection Swab 1 | 1485 | 1324 | 1174.25 | 6857016 | 3641489 | 8816031 | 8816.0 | 1556311 | 1591938 | 1514742 | 15147.4 |
| No enrichment, 2 hour infection Swab 2 | 1009 | 879 | | 12270780 | 12494840 | | | 1591938 | 1318782 | | |
| 1 hr enrichment, ½ hour infection Swab 1 | 180 | 172 | 154.75 | 3043784 | 3022935 | 2788381 | 2788.4 | 243195 | 250985 | 268535.3 | 2685.4 |
| 1hr enrichment, ½ hour infection Swab 2 | 138 | 129 | | 3022935 | 2063869 | | | 287315 | 292646 | | |

*Used 1000 RLU as background value

**Used 100 RLU as background value

FIG. 4

Table 5

| Sample | Infection Time | Hygenia RLU (1.2mL) | | | GloMax 20/20 RLU (1mL) | | | | GloMax 96-well RLU (150ul of 1.2mL) | | | |
|---|---|---|---|---|---|---|---|---|---|---|---|---|
| | | Run 1 | Run 2 | Avg. | Run 1 | Run 2 | Avg. | S/B* | Run 1 | Run 2 | Avg. | S/B** |
| Sample 21 | 30 min | 164 | 175 | 151.5 | 5948962 | 6013964 | 5580377 | 5580.377 | 547613 | 577622 | 499504.75 | 4995.048 |
| | 30 min | 131 | 136 | | 5136969 | 5221614 | | | 423329 | 449455 | | |
| | 2 hours | 7946 | 7867 | 7804.75 | 1.92E+08 | 1.9E+08 | 1.88E+08 | 187618.9 | 9095050 | 9428027 | 8678287.25 | 86782.87 |
| | 2 hours | 7599 | 7807 | | 1.89E+08 | 1.79E+08 | | | 8045154 | 8144918 | | |
| Sample 24 | 30 min | 0 | 0 | 0 | 2030 | 1950 | 1959.5 | 1.9595 | 179 | 188 | 181 | 1.81 |
| | 30 min | 0 | 0 | | 1930 | 1928 | | | 181 | 176 | | |
| | 2 hours | 213 | 304 | 243.75 | 2864579 | 2798654 | 2714867 | 2714.867 | 302943 | 263155 | 242337 | 2423.37 |
| | 2 hours | 223 | 235 | | 2548723 | 2647512 | | | 209433 | 193817 | | |
| Sample 26 | 30 min | 1 | 1 | 1 | 8229 | 8314 | 7717.5 | 7.7175 | 777 | 779 | 755 | 7.55 |
| | 30 min | 1 | 1 | | 7149 | 7178 | | | 741 | 723 | | |
| | 2 hours | 6432 | 6301 | 6017.75 | 1.28E+08 | 1.27E+08 | 1.25E+08 | 125323.5 | 13247709 | 12781102 | 14413062 | 144130.6 |
| | 2 hours | 5556 | 5782 | | 1.22E+08 | 1.23E+08 | | | 15946914 | 15676523 | | |

*Used 1000 for background
**Used 100 for background

FIG. 6

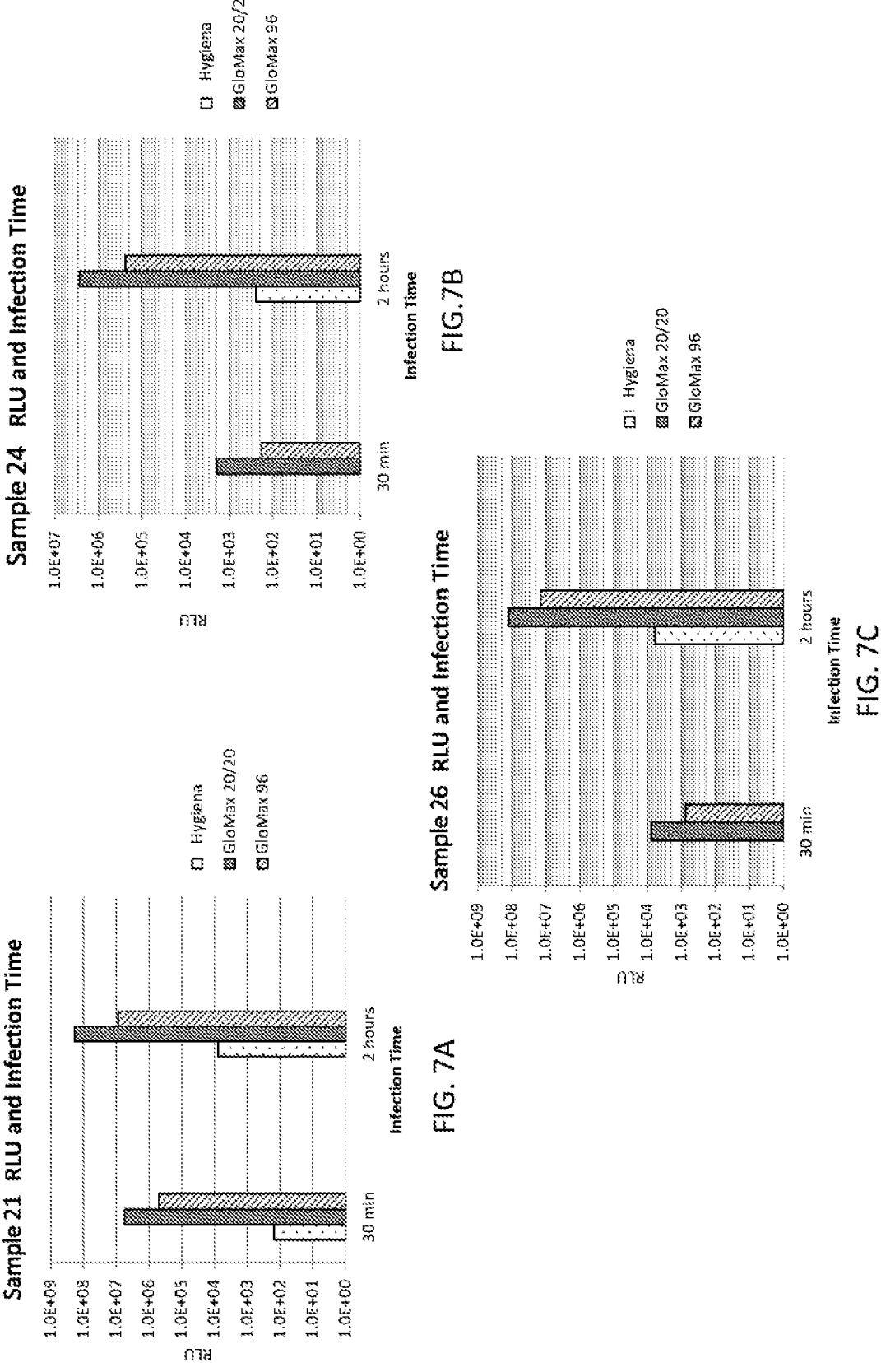

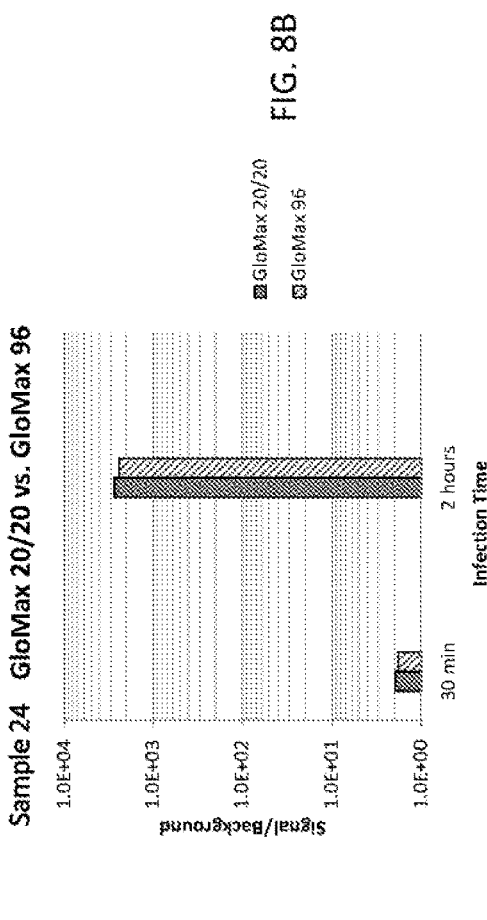
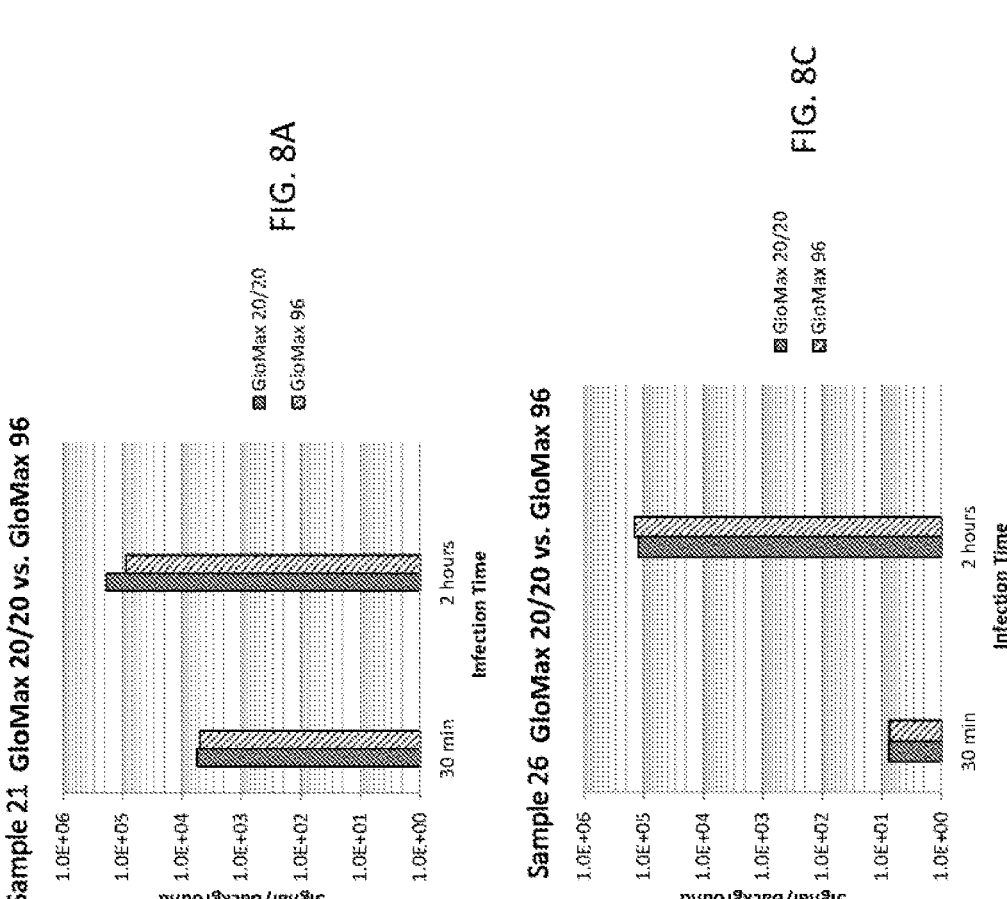

| Sample | Standard Assay – 24HR Enrichment, 4HR Injection (RLU) | GloMax (150ul of 1.2mL), 1 HR Injection (RLU) | Hygiena Handheld (1.2 mL), 1 HR Injection | Plating Confirmation? |
|---|---|---|---|---|
| 1 | 135 | 640 | 0 | NEG |
| 2 | 25868765 | 6664126 | 648 | POS |
| 3 | 562 | 106 | 0 | NEG |
| 4 | 45715742 | 10527167 | 783 | POS |
| 5 | 562 | 639 | 0 | NEG |
| 6 | 46897290 | 13604638 | 2437 | POS |
| 7 | 73017 | 1380 | 2 | POS |
| 8 | 223748 | 20567 | 35 | POS |
| 9 | 512 | 586 | 0 | NEG |
| 10 | 8229 | 1223 | 1 | POS |
| 11 | 6352 | 842 | 1 | POS |
| 12 | 33559 | 9083 | 7 | POS |
| 13 | 261 | 792 | 1 | NEG |
| 14 | 75024856 | 1837792 | 5441 | POS |
| 15 | 44634906 | 3004142 | 4151 | POS |
| 16 | 128 | 390 | 2 | NEG |
| 17 | 5554964 | 5620934 | 969 | POS |
| 18 | 92380016 | 1250344 | 6271 | POS |
| 19 | 86 | 597 | 2 | NEG |
| 20 | 492244 | 40464 | 64 | POS |
| 21 | 2668696 | 243893 | 368 | POS |
| 22 | 3280788 | 277796 | 195 | POS |
| 23 | 755.0052 | 405592 | 131 | POS |
| 24 | 98918810 | 1467343 | 975 | POS |
| 25 | 5296674 | 673373 | 202 | POS |
| 26 | 720 | 652 | 7 | NEG |
| 27 | 127035 | 1121685 | 556 | POS |
| 28 | 554491 | 206992 | 153 | POS |
| 29 | 642295 | 208947 | 157 | POS |
| 30 | 96285753 | 95885327 | 6498 | POS |
| 31 | 3941028 | 929674 | 786 | POS |
| 32 | 778 | 783 | 2 | NEG |
| 33 | 1998160 | 307865 | 228 | POS |
| 34 | 607 | 655 | 2 | NEG |
| 35 | 682 | 1340 | 2 | NEG |
| 36 | 80930274 | 5287746 | 5403 | POS |

FIG. 9

| Sample | GloMax (150ul of 1.2mL) | 3M Handheld (1.2 mL) | Hygiena Handheld (1.2 mL) |
|---|---|---|---|
| 1 | 150639 | 126399 | 278 |
| 2 | 1601 | 146 | 0 |
| 3 | 260334 | 138251 | 707 |
| 4 | 5227791 | 290340 | 1644 |
| 5 | 1402865 | 514051 | 1934 |
| 6 | 1814 | 157 | 2 |
| 7 | 4056691 | 201626 | 944 |
| 8 | 1460 | 146 | 2 |
| 9 | 530939 | 231426 | 1609 |
| 10 | 634884 | 300458 | 858 |
| 11 | 5613560 | 383552 | 1380 |
| 12 | 847341 | 490712 | 2394 |
| 13 | 355235 | 170642 | 459 |
| 14 | 1668857 | 591395 | 3601 |
| 15 | 1052748 | 512452 | 1659 |
| 16 | 141908 | 121216 | 359 |
| 17 | 1047 | 67 | 3 |
| 18 | 448721 | 260046 | 1574 |
| 19 | 678726 | 336346 | 1831 |
| 20 | 1056815 | 540753 | 1687 |
| 21 | 8890054 | 557789 | 3436 |
| 22 | 6205623 | 469794 | 1596 |
| 23 | 6402621 | 355698 | 1315 |
| 24 | 1585 | 750 | 5 |
| 25 | 869 | 109 | 4 |
| 26 | 12665555 | 593370 | 6189 |
| 27 | 5609521 | 455881 | 1860 |
| 28 | 4856627 | 346393 | 1908 |
| 29 | 16684520 | 423541 | 5122 |
| 30 | 10868815 | 595188 | 2516 |

FIG. 10

Phage

26

Swab

22

24

Media Free
Substrate

20

Phage

Polystyrene Bead

Media
Substrate

Phage

26

Swab

22

24

Media
Substrate

20

200

Stop-lock

Swab

Media Free
Phage
Substrate

Stop-lock

Polystyrene Bead

Media
Phage
Substrate

Stop-lock

46

Swab

Media
Phage
Substrate

40

42
44

400

Overnight Enrichment Sample → Swab enriched sample → Infection → Read

SELF-CONTAINED APPARATUS AND SYSTEM FOR DETECTING MICROORGANISMS

CROSS REFERENCE TO RELATED APPLICATION

The present application claims priority to U.S. provisional Application Nos. 62/777,473, filed on Dec. 10, 2018, and 62/798,980, filed on Jan. 30, 2019. The disclosures of U.S. application Ser. Nos. 13/773,339, 14/625,481, 15/263,619, 15/409,258, 16/298,695 and U.S. provisional Application Nos. 62/616,956, 62/628,616, 62/661,739, 62/640,793, and 62/798,980 are hereby incorporated by reference in their entirety herein.

FIELD OF THE INVENTION

The invention relates to methods, apparatuses, devices, and systems for detection of microorganism of interest using recombinant bacteriophages.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Detection of microorganisms is a high priority for the Food and Drug Administration (FDA) and Centers for Disease Control (CDC) given outbreaks of life-threatening or fatal illness caused by ingestion of food contaminated with certain microorganisms, e.g., *Staphylococcus* spp., *Escherichia coli* or *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, to-date, methods reducing the time requirement have drawbacks. For example, techniques involving direct immunoassays or gene probes generally require an overnight enrichment step in order to obtain adequate sensitivity, and therefore lack the ability to deliver same-day results. Polymerase chain reaction (PCR) tests also include an amplification step and therefore are capable of both very high sensitivity and selectivity; however, the sample size that can be economically subjected to PCR testing is limited. Dilute bacterial suspensions capable of being subjected to PCR will be free of cells and therefore purification and/or lengthy enrichment steps are still required.

The time required for traditional biological enrichment is dictated by the growth rate of the target bacterial population of the sample, by the effect of the sample matrix, and by the required sensitivity. In practice, most high sensitivity methods employ an overnight incubation and take about 24 hours overall. Due to the time required for cultivation, these methods can take up to three days, depending upon the organism to be identified and the source of the sample. This lag time is generally unsuitable as such delays allow contaminated food or water or other products to make its way into livestock or humans. In addition, increases in antibiotic-resistant bacteria and biodefense considerations make rapid identification of bacterial pathogens in water, food, and clinical samples critical priorities worldwide.

Therefore, there is a need for more rapid, simple and sensitive detection and identification of microorganisms, such as bacteria and other potentially pathogenic microorganisms.

SUMMARY

Embodiments of the invention comprise devices, compositions, methods, apparatuses, systems, and kits for the detection of microorganisms. The invention may be embodied in a variety of ways.

Aspects of the invention comprise devices for facilitating ease and simplicity of microorganism detection. Described herein is an apparatus or device for performing an assay to detect a microorganism in a test sample using recombinant bacteriophage.

In one aspect, the present invention utilizes the high specificity of bacteriophage that can bind microorganisms to detect low levels of a microorganism. In some embodiments, the method detects as few as 10, 9, 8, 7, 6, 5, 4, 3, 2, or a single bacterium in a sample of a standard size for the food safety industry. In other embodiments, the sample is first incubated in conditions favoring growth for an enrichment period of 9 hours or less, 8 hours or less, 7 hours or less, 6 hours or less, 5 hours or less, 4 hours or less, 3 hours or less, or 2 hours or less. In some embodiments, the sample is not enriched prior to incubation with recombinant bacteriophage.

In some embodiments, the recombinant bacteriophage is genetically modified to include a reporter gene as previously described. In additional embodiments the recombinant bacteriophage is derived from bacteriophage specific to the microorganism to be detected. For example, the recombinant bacteriophage may be derived from any of the following bacteriophages: *Salmonella* phage SPN1S, *Salmonella* phage 10, *Salmonella* phage epsilon15, *Salmonella* phage SEA1, *Salmonella* phage Spn1s, *Salmonella* phage P22, *Listeria* phage LipZ5, *Listeria* phage P40, *Listeria* phage vB_LmoM_AG20, *Listeria* phage P70, *Listeria* phage A511, *Staphylococcus* phage P4W, *Staphylococcus* phage K, *Staphylococcus* phage Twort, *Staphylococcus* phage SA97, or *Escherichia coli* O157:H7 phage CBA120.

In some embodiments, the recombinant bacteriophage may be stabilized or preserved. For example, the recombinant bacteriophage may be lyophilized.

In certain embodiments, the reporter generates an indicator moiety. In certain embodiments the indicator moiety can generate an intrinsic signal. In other embodiments the indicator moiety comprises an enzyme that generates signal upon reaction with substrate. In yet other embodiments, the indicator moiety comprises a cofactor that generates signal upon reaction with one or more additional signal producing components. For example, the indicator moiety comprises at least one of a fluorophore, a fluorescent protein, a particle, and an enzyme. The enzyme may comprise at least one of a luciferase, a phosphatase, a peroxidase, and a glycosidase. The luciferase gene can be a naturally occurring gene, such as *Oplophorus* luciferase, Firefly luciferase, Lucia luciferase, or Renilla luciferase, or it can be a genetically engineered gene.

Some embodiments of the invention comprise a device or apparatus for performing the detection method. In some embodiments a device may include separate compartments. In some embodiments separate compartments of a device may be configured to allow a user to combine the contents from different compartments at various stages of the detection method. For example, the sample to be tested may be combined with a bacteriophage in one compartment and allowed to incubate for some period of time before being added to the contents of another compartment of the device, such as a substrate. In such embodiments the substrate may react with any reporter (or indicator moiety) produced as a result of infection by the recombinant bacteriophage (e.g., if the target microorganism is present in the sample).

Some embodiments include a device comprising a first compartment comprising a recombinant bacteriophage having a genetic construct inserted into a bacteriophage genome, wherein the construct comprises a promoter and an indicator gene; and a second compartment comprising a signal detecting component, wherein the signal detecting component facilitates detection of the indicator gene product produced as a result of infecting the sample with the recombinant bacteriophage. In some embodiments, the signal detecting component is a substrate and the indicator gene encodes an enzyme. In some embodiments, the enzyme is a luciferase.

In some embodiments, the apparatus comprises a first compartment comprising recombinant bacteriophage, an inlet/portal for adding a portion of a test sample to the recombinant bacteriophage, and a second compartment comprising a substrate or other paired reagent and wherein the method further comprises adding the substrate from the second compartment to the sample, concurrently with or after adding the recombinant bacteriophage. In some embodiments, wherein the apparatus comprises a third compartment. The third compartment can, for example, comprise growth media for enriching a sample. In other embodiments, the apparatus is free of media.

In some embodiments, the apparatus further comprises a second compartment comprising a substrate, and wherein detecting the indicator gene product is by contacting the indicator gene product with a substrate. In some embodiments, the solid support is a bead. In some embodiments, the solid support comprises polyethylene (PE), polypropylene (PP), polystyrene (PS), polylactic acid (PLA) and polyvinyl chloride (PVC). In some embodiments, the solid support is dry prior to contacting the sample. In some embodiments, the solid support is soaked in media prior to contacting the sample. In some embodiments, the solid support that has captured the one or more organisms is incubated with the growth media in the third compartment before contacting with the recombinant bacteriophage.

In some embodiments, the solid support is coated with a cell binding component that binds with high affinity to the microorganism of interest in the sample. This allows the more bacteria binding to the solid support and increase assay sensitivity and specificity. In other embodiments, the solid support is coated with an antibody capable of binding the microorganism of interest.

In some embodiments, the first compartment comprises a seal, and wherein contacting the recombinant bacteriophage with the sample is by breaking the seal, wherein the breakage of the seal causes the recombinant bacteriophage from the first compartment to be in contact with the sample and infect the one or more microorganisms in the sample, thereby producing indicator gene product (indicator protein). In further embodiments, the apparatus comprises a stop-lock for phased mixing of the media, the recombinant bacteriophage, and the substrate with the sample.

In some embodiments, the indicator gene product comprises at least one of a fluorophore, a fluorescent protein, a particle, and an enzyme. In some embodiments, the enzyme comprises at least one of a luciferase, a phosphatase, a peroxidase, and a glycosidase. In some embodiments, the luciferase is a genetically engineered luciferase. In some embodiments, the sample is a food, environmental, water, commercial, or clinical sample.

In another aspect, the method to detect one or more microorganism of interest in a sample comprising the steps of: contacting. the sample with a solid support of an apparatus, wherein the solid support captures the one or more microorganisms in the sample, if present, wherein the apparatus comprises: a first compartment comprising recombinant bacteriophage having a genetic construct inserted into a bacteriophage genome, wherein the construct comprises a promoter and an indicator gene; contacting the recombinant bacteriophage from the first compartment with the sample such that the recombinant bacteriophage infect the one or more microorganisms in the sample, thereby producing indicator gene product, and detecting the indicator gene product.

In some embodiments, the method comprising incubating the solid support that has captured the one or more microorganisms of interest in the growth media for a time period before adding the recombinant bacteriophage. In some embodiments, the incubation is 0-2 hours. In some embodiments, wherein the bacteriophage has been in contact with the sample for 0.5-3 hours before detecting the indicator gene product.

In some embodiments, the method detects as few as 10, 9, 8, 7, 6, 5, 4, 3, 2, or a single bacterium in a sample of a standard size for the food safety industry. In some embodiments, the sample comprises meat or vegetables. In some embodiments, the sample is a food, water, dairy, environmental, commercial, or clinical sample.

In some embodiments, the sample is first incubated in conditions favoring growth for an enrichment period of 9 hours or less, 8 hours or less, 7 hours or less, 6 hours or less, 5 hours or less, 4 hours or less, 3 hours or less, or 2 hours or less.

Additional embodiments include systems and kits for detecting microorganisms such as *Listeria, Salmonella, Staphylococcus,* or *E. coli* O157:H7, comprising a recombinant bacteriophage. Some embodiments further include a substrate for reacting with an indicator moiety of the recombinant bacteriophage. These systems or kits can include features described for the bacteriophage, compositions, and methods of the invention. In still other embodiments, the invention comprises non-transient computer readable media for use with methods or systems according to the invention.

In another aspect, this disclosure provides a system for detecting microorganism of interest in a sample comprising: an apparatus, which comprises: a first compartment comprising recombinant bacteriophage having a genetic construct inserted into a bacteriophage genome, wherein the construct comprises a promoter and an indicator gene; and a signal detecting component, wherein the signal detecting component can detect the indicator gene product produced from infecting the sample with the recombinant bacteriophage. In some embodiments, the signal detecting component is a handheld luminometer.

BRIEF DESCRIPTION OF THE FIGURES

The present invention may be better understood by referring to the following non-limiting figures.

FIG. 2 shows the results of detecting *L. monocytogenes* culture using one embodiment of a self-contained apparatus with a swab as a solid support. The signals corresponding to the presence of the bacteria was detected by Hygiena, GloMax, and GloMax 20/20 luminometers. Table 1 shows results from log phase culture and Table 2 shows results from overnight culture.

FIG. 3A shows measurements of signals detected using Hygiena. Swabs were inoculated with log phase cells at the indicated CFU level. Sample was immediately infected with *Listeria* phage cocktail for 4 hours. Substrate was added and samples were read on the Hygiena Luminometer. A signal of >10 RLU is considered positive. With this method, approximately 25,000 CFU is required to generate a positive result.

FIG. 3B shows the measurements of signals detected using GloMax 20/20 and GloMax (a.k.a., GloMax 96) luminometers. Swabs were inoculated with log phase cells at the indicated CFU level. Sample was immediately infected with *Listeria* phage cocktail for 4 hours. Substrate was added and samples were read on either the GloMax 20/20 (1 mL of sample) or GloMax (150 μl of sample) Luminometers. A signal/background ratio of >3.0 is considered positive. With this method, approximately 5,000 CFU is required to generate a positive result.

FIG. 4 shows the results of detecting *Salmonella* in ground turkey that has been inoculated with *Salmonella*. Table 3 shows uninoculated control sample, and Table 4 shows inoculated turkey sample. The tests were repeated with varying incubation and infection time.

FIG. 6A shows that *Salmonella*-inoculated turkey samples were detected as positive with every incubation and infection time tested. The turkey sample was grown for 24 hours at 41° C. after inoculation before testing with the methods disclosed in the application. For relative signal: 0 HR incubation, 2 HR infection >1 HR incubation, 0.5 HR infection >0 HR incubation, 0.5 HR infection. In addition, comparison of RLU signal shows that the GloMax luminometers have a much higher signal that that of the Hygiena luminometer.

FIG. 5B shows that detecting using GloMax 20/20 and GloMax luminometers produced similar signal/background ratios for the same samples. Although the GloMax 20/20 had a greater signal (FIG. 5A), the background was significantly higher than that with the GloMax. Thus when determining the signal/background, the two luminometers perform similarly.

FIG. 6 shows data for detecting *Salmonella* in three turkey samples (samples 21, 24, and 26) that had been inoculated with *Salmonella* before the assays using the self-contained apparatus. The samples were infected for different duration of time as indicated before detection of the signal.

FIGS. 7A-7C are plots generated from the data shown in FIG. 6. FIGS. 7A-7C show results of the experiments in which three inoculated ground turkey samples were enriched for 24 hours and swab samples were taken and assayed. Sample 24 (FIG. 7B) and 26 (FIG. 7C) did not show signal on Hygiena handheld luminometer for samples that had 30 min phage infection, but did for sample that had 2 hour infection. The GloMax 20/20 and GloMax luminometer generated relatively low signals.

FIGS. 8A-8C are plots generated from the data shown in FIG. 6. The plots show both GloMax 20/20 and GloMax were able to detect Sample 21 (FIG. 8A) and 26 (FIG. 8B) as positive with 30 minute infection (signal/background ratio of >3.0 is positive), however Sample 24 (FIG. 8C)

required a 2 hour infection to show a positive result. The GloMax 20/20 and GloMax luminometer results were similar.

FIG. 9 shows data for detecting *L. monocytogenes* environmental sponge samples from inoculated surfaces and enriched for 24 hours.

FIG. 10 shows detecting microorganisms in *Salmonella*-inoculated turkey samples using the apparatus. The signals were measured using three different luminometers: GloMax, 3M, and Hygiena.

Figure 11C:
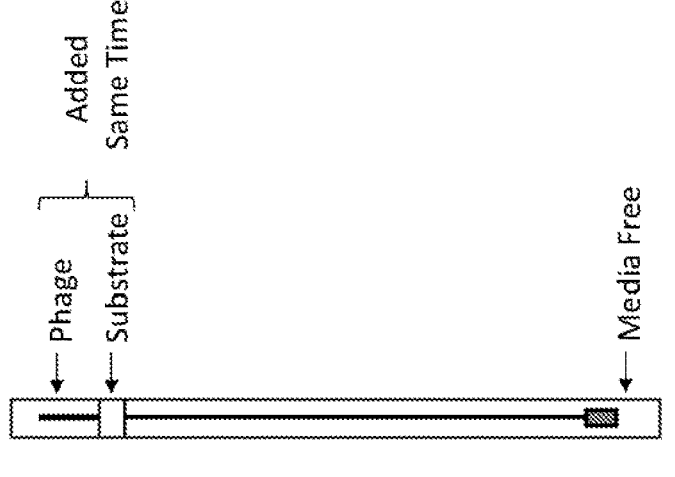
Figure 11B:
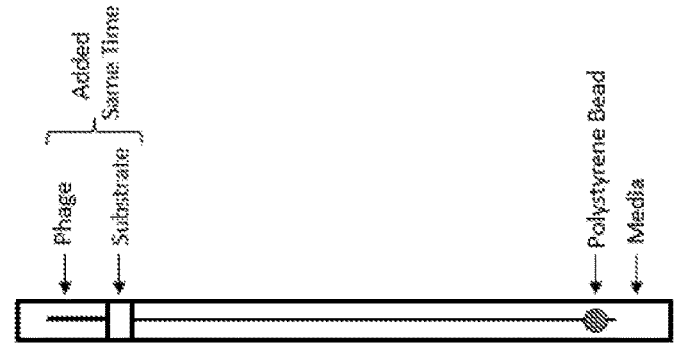
Figure 11A:
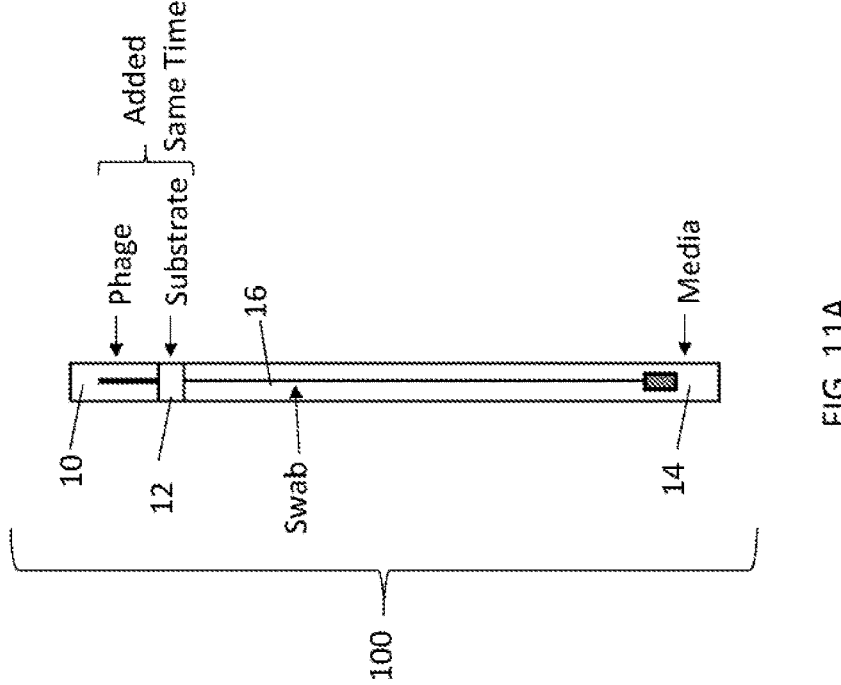

FIGS. 11A, 11B, and 11C depict a view of one embodiment of a self-contained apparatus system for detecting microorganisms, having a swab (FIG. 11A) or a bead (FIG. 11B) inserted into a container comprising three compartments. Each compartment is separated by a snap action seal. The first compartment contains phage, the second compartment contains substrate, and the third compartment contains media. In some embodiments the solid support is a swab. In some embodiments, the device is free of media (FIG. 11C).

Figure 12C:
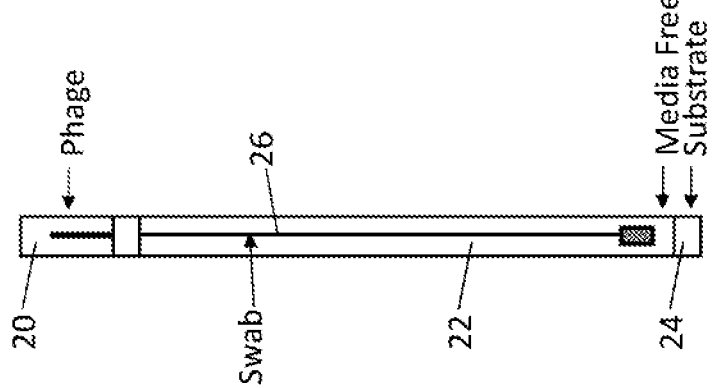
Figure 12B:
Figure 12A:
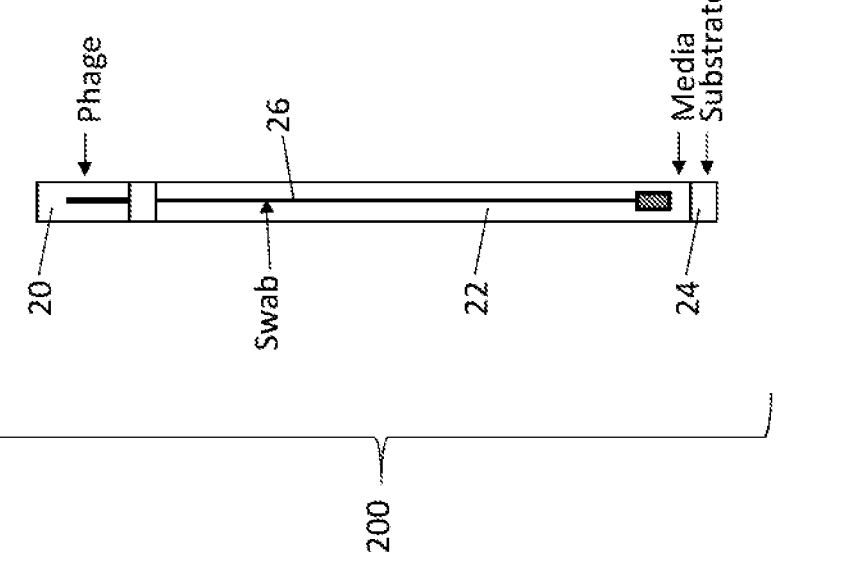

FIGS. 12A, 12B and 12C depict a view of one embodiment of a self-contained apparatus system for detecting microorganisms, having a swab (FIG. 12A) or a bead (FIG. 12B) inserted into a container comprising three compartments. Each compartment is separated by a snap action seal. The first compartment contains phage, the second compartment contains media, and the third compartment contains substrate. After incubation with the phage and media, the seal separating the second and third compartment may be broken. In some embodiments the solid support is a swab. In some embodiments, the device is free of media (FIG. 12C).

Figure 13C:
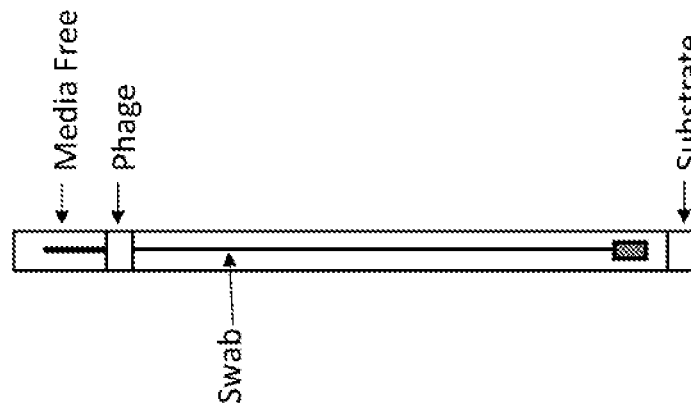
Figure 13B:
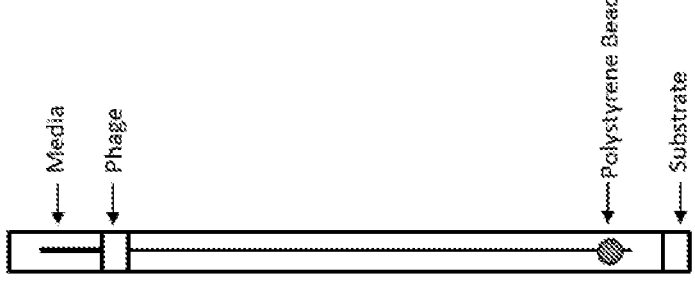
Figure 13A:
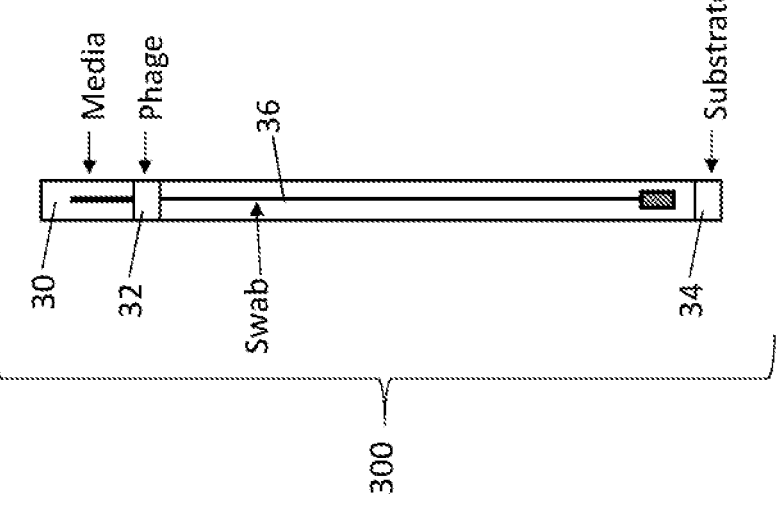

FIGS. 13A, 13B, and 13C depict a view of one embodiment of a self-contained apparatus system for detecting microorganisms, having a swab (FIG. 13A) or a bead (FIG. 13B) inserted into a container comprising three compartments. Each compartment is separated by a snap action seal. The first compartment contains media, the second compartment contains phage, and the third compartment contains substrate. In some embodiments the solid support is a swab. In some embodiments, the device is free of media (FIG. 13C).

Figure 14C:
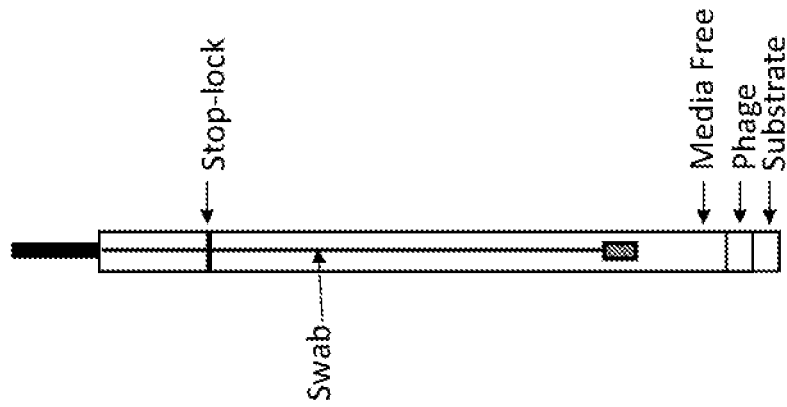
Figure 14B:
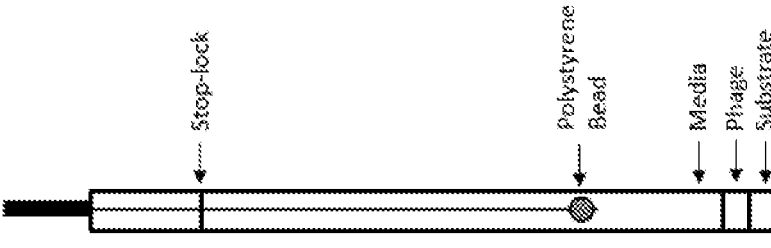
Figure 14A:
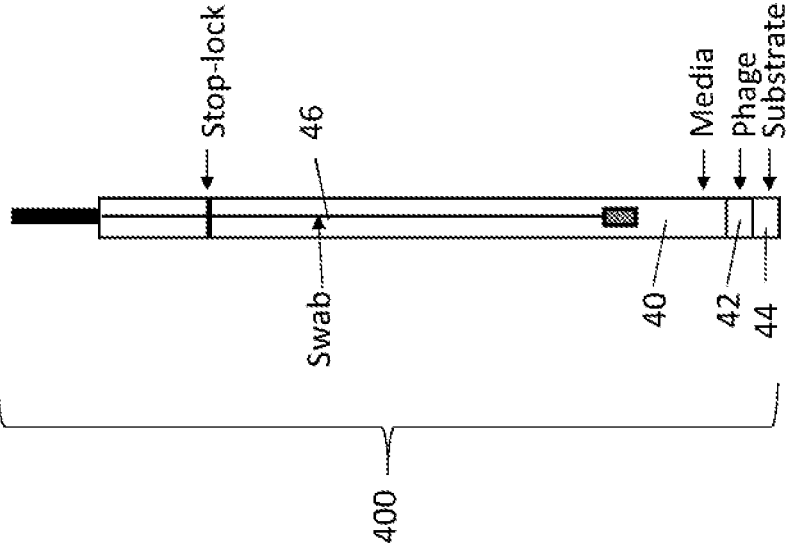

FIGS. 14A, 14B, and 14C depict a view of one embodiment of a self-contained apparatus system for detecting microorganisms, having a swab (FIG. 14A) or a bead (FIG. 14B) inserted into a container comprising three compartments. Each compartment is separated by a snap action seal. The first compartment contains media, the second compartment contains phage, and the third compartment contains substrate. The apparatus has a stop-lock mechanism for phased mixing of reagents. In some embodiments the solid support is a swab. In some embodiments, the device is free of media (FIG. 14C).

Figure 15C:
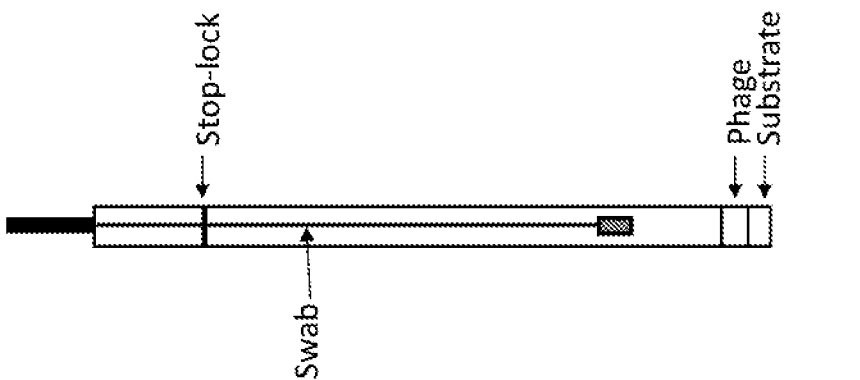
Figure 15B:
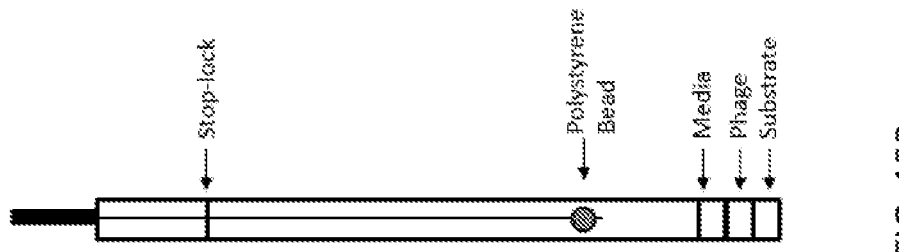
Figure 15A:
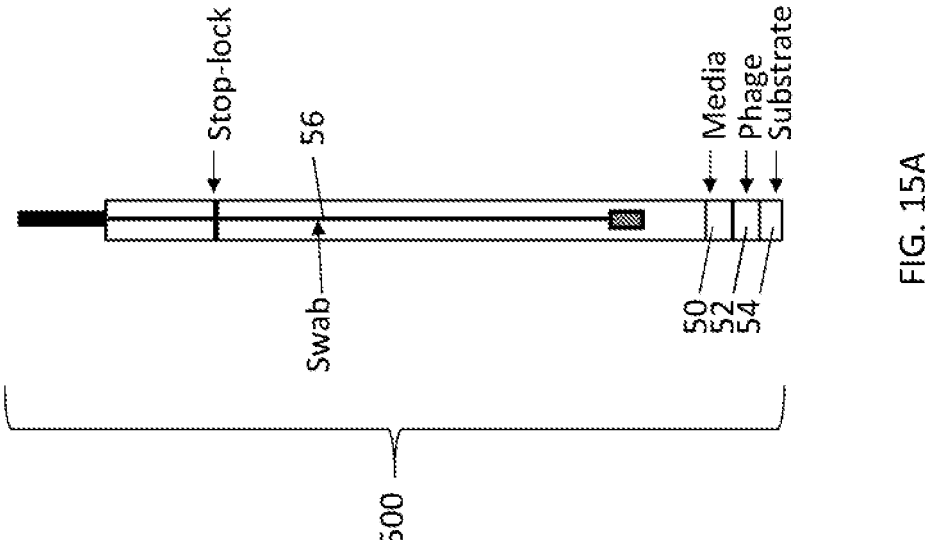

FIGS. 15A, 15B, and 15C depict a view of one embodiment of a self-contained apparatus system for detecting microorganisms, having a swab (FIG. 15A) or a bead (FIG. 15B) inserted into a container comprising three compartments. Each compartment is separated by a snap action seal. The first compartment contains media, the second compartment contains phage, and the third compartment contains substrate. The apparatus has a stop-lock mechanism for phased mixing of reagents. In some embodiments the solid support is a swab. In some embodiments, the device is free of media (FIG. 15C).

Figure 16:
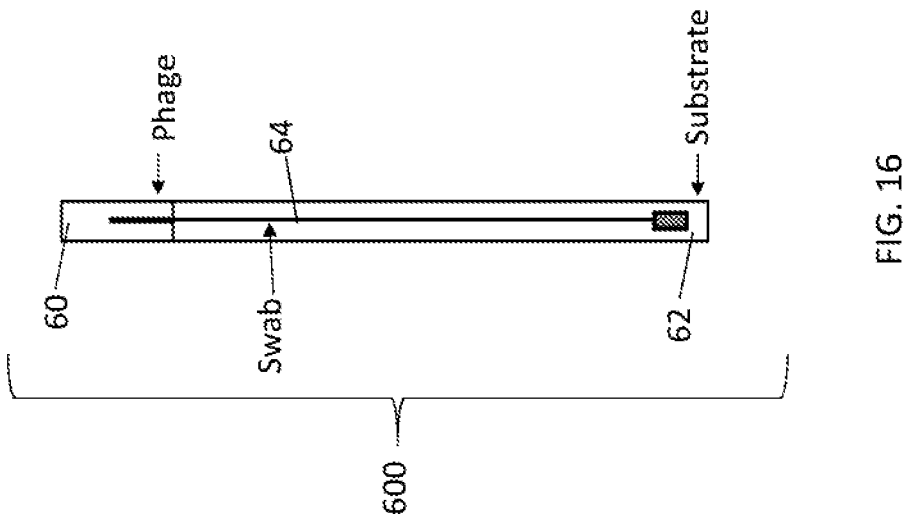

FIG. 16 depicts a view of one embodiment of a self-contained apparatus system for system for detecting microorganisms, having a swab inserted into a container comprising two compartments. Each compartment is separated by a snap action seal. The first compartment contains phage and the second compartment contains substrate. In some embodiments the solid support is a swab.

Figure 17:
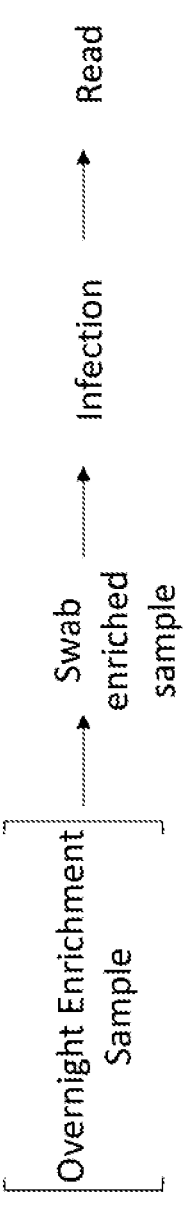

FIG. 17 depicts a flow diagram of an embodiment utilizing a self-contained apparatus system for detecting microorganisms.

DETAILED DESCRIPTION OF THE INVENTION

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well-known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate or lateral flow strip).

The term "indicator" or "indicator moiety" or "detectable moiety" or "detectable biomolecule" or "reporter" or "label" refers to a molecule that provides a signal that can be measured in a qualitative or quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase, HRP, or AP). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves.

As used herein, "culture enrichment", "culturing for enrichment", "cultured for enrichment", or "culture for enrichment", refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for short periods of time may be employed in some embodiments of methods described herein, but is not necessary and is for a much shorter period of time than traditional culturing for enrichment, if it is used at all.

As used herein "recombinant" refers to genetic (i.e., nucleic acid) modifications as usually performed in a laboratory to bring together genetic material that would not otherwise be found. This term is used interchangeably with the term "modified" herein.

As used herein "RLU" refers to relative light units as measured by a luminometer (e.g., GLOMAX® 96) or similar instrument that detects light. For example, the detection of the reaction between luciferase and appropriate substrate (e.g., NANOLUC® with NANO-GLO®) is often reported in RLU detected.

Overview

The present invention utilizes the high specificity of recombinant bacteriophage that can bind to a particular microorganism with high affinity to detect the presence of and/or quantify the specific microorganism in the sample.

Disclosed herein are compositions, methods, kits, and systems that demonstrate surprising sensitivity and speed for detection of a microorganism of interest in test samples (e.g., food, water, dairy, environmental, commercial, clinical, or other biological samples) using assays performed without culturing for enrichment, or in some embodiments with minimal incubation times during which microorganism could potentially multiply. These compositions, methods, kits, and systems allow detection of microorganisms to be achieved in a shorter timeframe than was previously thought possible.

Embodiments of the compositions, methods, kits, and system of the invention can be applied to detection of a variety of microorganisms (e.g., bacteria, fungi, yeast) in a variety of circumstances, including but not limited to, detection of pathogens from food, water, dairy, environmental, commercial, clinical, or other biological samples. The recombinant bacteriophage based detection embodiments disclosed herein may be adapted to any bacteria or other microorganism of interest (e.g., pathogenic microorganisms) for which a specific bacteriophage is available that does not recognize microorganisms for which detection is not of interest. The methods of the present invention provide high detection sensitivity and specificity rapidly and without the need for traditional biological enrichment (e.g., culturing). Thus, a variety of microorganisms may be detected using the methods of the invention.

Embodiments of the methods and systems of the invention can be applied to detection and quantification of a variety of microorganisms (e.g., bacteria, fungi, yeast) in a variety of circumstances, including but not limited to detection of pathogens from food, water, dairy, environmental, commercial, clinical, or other biological samples. The methods of the present invention can rapidly provide high detection sensitivity and specificity without the need for traditional biological enrichment (e.g., culturing), which is a surprising aspect as all available methods with the desired sensitivity and specificity require culturing.

Also disclosed herein are systems and methods that uses an apparatus to detect microorganisms in test samples (e.g., food, water, dairy, environmental, commercial, clinical, or other biological samples). The method uses a self-contained apparatus that comprise a solid support, that can be used to collect sample. The apparatus further comprises a first compartment comprising bacteriophage having a genetic construct inserted into the bacteriophage genome, wherein the construct comprises a promoter and an indicator gene. The method comprises contacting the recombinant bacteriophage from the first compartment with the sample such that the recombinant bacteriophage infect one or more microorganisms in the sample thereby producing an indicator gene product ("indicator"), and detecting the indicator. In some aspects, the apparatus further comprises a second compartment, which contains a substrate specific for detecting the indicator. In some embodiments, the method further comprises contacting the sample that has been infected by the bacteriophage with the substrate, whereby detecting the indicator. In these embodiments, each compartment is separated from the immediately adjacent compartment by a snap action seal, which upon breakage, allows the content of the compartments to exit the compartment and mix with contents from the sample or contents from other compartments. For example, a user can break the snap action seal such that the recombinant bacteriophage from the first compartment contacts the sample on the solid support, thereby infecting microorganisms that bind thereon. Upon infection of the microorganisms, the indicator gene is expressed to produce an indicator protein, which can be detected by various detection devices. The presence of the signals indicates the presence of the microorganisms in the sample.

Embodiments of the apparatus, compositions, methods, kits, and system of the invention can be applied to detection of a variety of microorganisms (e.g., bacteria, fungi, yeast) in a variety of circumstances, including but not limited to, detection of pathogens from food, water, dairy, environmental, commercial, clinical, or other biological samples. The detection embodiments disclosed herein may be adapted to any bacteria or other microorganism of interest (e.g., pathogenic microorganisms) for which a specific recombinant bacteriophage is available that does not recognize other microorganisms that are not of interest. The methods of the present invention provide high detection sensitivity and specificity rapidly and without the need for traditional biological enrichment (e.g., culturing). This is a surprising aspect as all available methods with the desired sensitivity and specificity require culturing. The detection of microorganisms in a sample using the self-contained apparatus, which houses reagents required for detecting the microorganism in separate compartments until the time of detection, is convenient and efficient. The apparatus is easy to use and does not require extensive training.

Samples

Each of the embodiments of the compositions, methods, kits, and systems of the invention allows for the rapid detection and/or quantification of microbes in a sample. For example, methods according to the present invention can be performed in a shortened time period with superior results.

In certain embodiments, a recombinant bacteriophage is used to detect microorganisms of interest. Microorganisms that can be detected by the compositions, methods, kits and systems of the present invention include pathogens that are of commercial, medical, or veterinary concern. Any microorganism for which a recombinant bacteriophage specific for the particular microbe has been identified can be detected by the methods of the present invention. Those skilled in the art will appreciate that there is no limit to the application of the present methods other than the availability of the necessary recombinant bacteriophage/microbe pairs.

Bacterial cells detectable by the present invention include, but are not limited to, bacterial cells that are food- or water-borne pathogens. Bacterial cells detectable by the present invention include, but are not limited to, all species of *Salmonella*, all strains of *Escherichia coli*, including, but not limited to *E. coli* O157:H7 (and other Shiga toxin- and enterotoxin-producing strains of *E. coli*), all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis*, *Brucella* spp., *Campylobacter jejuni*, *Chlamydia pneumoniae*, *Clostridium perfringens*, *Clostridium botulinum*, *Enterobacter* spp., *Klebsiella pneumoniae*, *Mycoplasma pneumoniae*, *Salmonella typhi*, *Salmonella typhimurium*, *Salmonella enteritidis*, *Shigella sonnei*, *Yersinia* spp., *Vibrio* spp. *Staphylococcus aureus*, and *Streptococcus* spp.

The sample may be an environmental or food or water sample. Some embodiments may include medical or veterinary samples. Samples may be liquid, solid, or semi-solid. Samples may be swabs of solid surfaces. Samples may include environmental materials, such as water samples, or the filters from air samples, or aerosol samples from cyclone collectors. Samples may be of beef, poultry, processed foods, milk, cheese, or other dairy products. Medical or veterinary samples include, but are not limited to, blood, sputum, cerebrospinal fluid, and fecal samples. In some embodiments, samples may be different types of swabs.

In some embodiments, samples may be used directly in the detection methods of the present invention, without preparation, concentration, or dilution. For example, liquid samples, including but not limited to, milk and juices, may be assayed directly. In other embodiments, samples may be diluted or suspended in solution, which may include, but is not limited to, a buffered solution or a bacterial culture medium. A sample that is a solid or semi-solid may be suspended in a liquid by mincing, mixing or macerating the solid in the liquid. In some embodiments, a sample should be maintained within a pH range that promotes recombinant bacteriophage attachment to the host bacterial cell. In some embodiments, the preferred pH range may be one suitable for bacteriophage attached to a bacterial cell. A sample should also contain the appropriate concentrations of divalent and monovalent cations, including but not limited to Na$^+$, Mg$^{2+}$, and K$^+$.

In some embodiments, the sample is maintained at a temperature that maintains the viability of any pathogen cell present in the sample. During steps in which bacteriophage, are attaching to bacterial cells, the sample may be maintained at a temperature that facilitates bacteriophage activity. Such temperatures are at least about 25° C. and no greater than about 45° C. In some embodiments the sample is maintained at about 37° C. In some embodiments the samples are subjected to gentle mixing or shaking during recombinant bacteriophage binding or infection.

Methods of Using Recombinant Bacteriophage for Detecting Microorganism

Methods for using recombinant bacteriophage to detect microorganisms of interest have previously been described. Assays may include various appropriate control samples. For example, control samples containing no recombinant bacteriophages and/or control samples containing recombinant bacteriophages without bacteria may be assayed as controls for background signal levels.

As noted herein, in certain embodiments, the invention may comprise methods of using recombinant bacteriophage for detecting microorganisms. The methods of the invention may be embodied in a variety of ways.

In some aspects, the invention comprises a method for detecting a microorganism of interest. The method may use a recombinant bacteriophage for detection of the microorganism of interest. For example, in certain embodiments, the microorganism of interest is a bacterium and the recombinant bacteriophage is derived from a bacteriophage that specifically recognizes the bacterium of interest. In certain embodiments, the method may comprise detection of a bacterium of interest in a sample by incubating the sample with a plurality of recombinant bacteriophage that can bind to the bacterium of interest. A plurality of recombinant bacteriophage bound to a single microorganism is any number greater than 1, but is preferably at least $5\times10^4$, or at least $1\times10^5$, or at least $1\times10^6$, or at least $1\times10^8$, or at least $1\times10^9$, or at least $1\times10^{10}$ recombinant bacteriophage.

In certain embodiments, the recombinant bacteriophage comprises an indicator moiety. The methods may comprise detecting the indicator moiety of the recombinant bacteriophage, wherein positive detection of the indicator moiety indicates that the bacterium of interest is present in the sample.

In some embodiments, the invention may comprise a method to detect as few as a single microorganism of interest in a sample comprising the steps of: incubating the sample with a plurality of recombinant bacteriophage that bind the microorganism of interest, wherein the recombinant bacteriophage comprises an indicator moiety and is contacted with the sample to be tested under conditions such that the plurality of recombinant bacteriophage bind the bacterium of interest; separating unbound recombinant bacteriophage from cell-bound recombinant bacteriophage; and detecting the indicator moiety resulting from infection of the bacterium, wherein positive detection of the indicator moiety indicates that the microorganism of interest is present in the sample. Embodiments may include incubating the sample with at least $5\times10^8$, or at least $5\times10^9$, or at least $5\times10^{10}$, or at least $5\times10^{11}$, or at least $5\times10^{12}$, or at least $5\times10^{13}$ recombinant bacteriophage.

In some embodiments, the detecting step will require addition of a substrate for the indicator enzyme to act on. The selection of a particular indicator is not critical to the present invention, but the indicator will be capable of generating a detectable signal either by itself, or be instrumentally detectable, or be detectable in conjunction with one or more additional signal producing components, such as an enzyme/substrate signal producing system.

In certain embodiments, the assay may be performed to utilize a recombinant bacteriophage to identify the presence of a specific microorganism. The assay can be modified to accommodate different sample types or sizes and assay formats. Embodiments employing recombinant bacteriophage of the invention may allow rapid detection of specific bacterial strains, with total assay times under 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, or 12 hours, depending on the sample type, sample size, and assay format. For example, the amount of time required may be somewhat shorter or longer depending on affinity of the recombinant bacteriophage and/or and types of bacteria to be detected in the assay, type and size of the sample to be tested, complexity of the physical/chemical environment, and the concentration of endogenous non-target bacterial contaminants.

Figure 1:
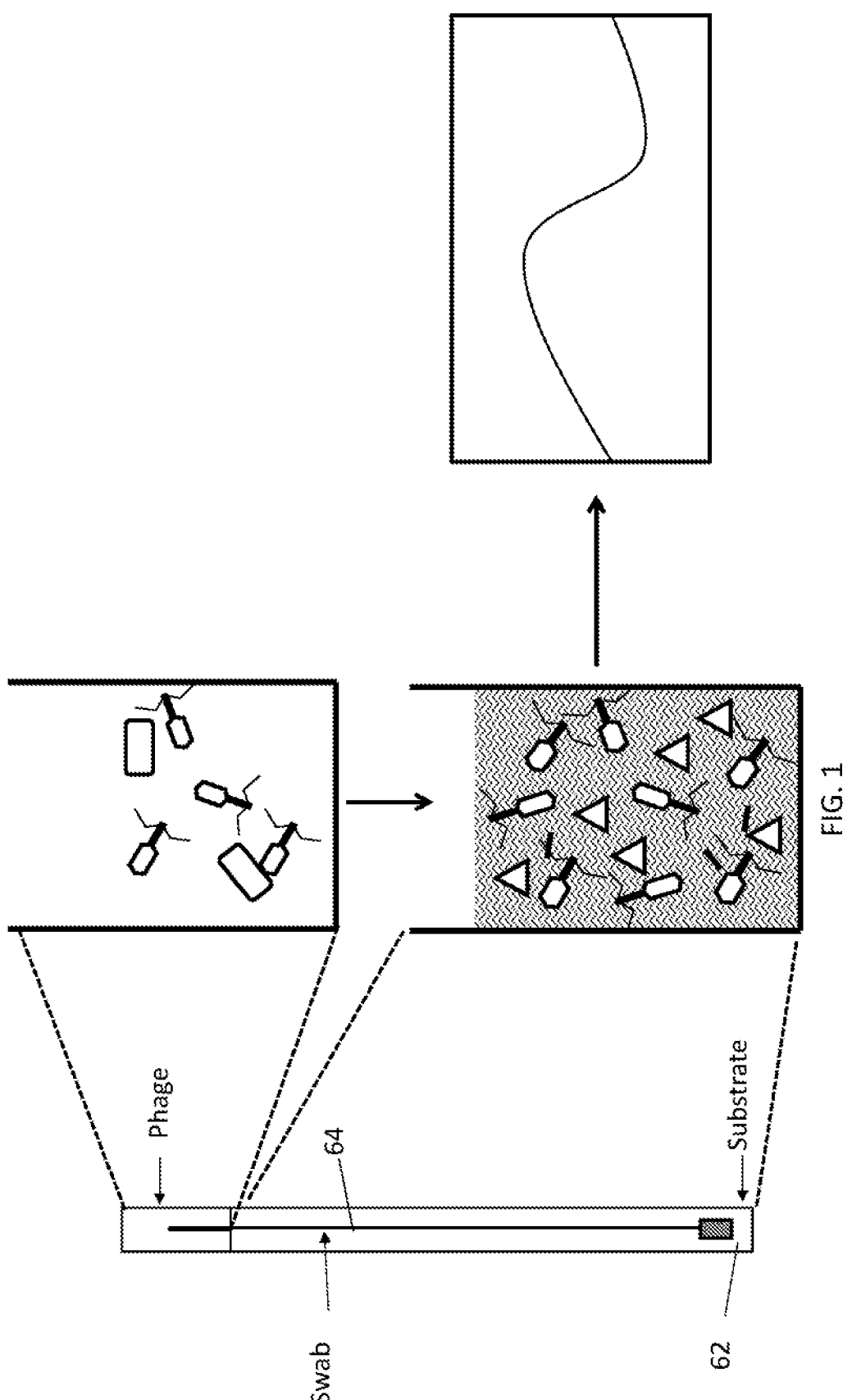
FIG. 1 shows one embodiment of a method for detecting a bacterium of interest using a recombinant bacteriophage.

FIG. 1 illustrates an embodiment of an assay for detecting a bacterium of interest using a recombinant bacteriophage according to an embodiment of the invention. A wide variety of configurations and steps for combining reagents are possible. In the embodiment illustrated here, aliquots of indicator phage (or lyophilized indicator phage) are contained in a first compartment of a device. A swab containing bacteria is introduced into the first compartment and incubated for a period of time (e.g., 45 minutes at 37° C.) sufficient for phage to replicate and generate soluble indicator (e.g., luciferase). The seal between the first compartment containing soluble indicator and phage and a second compartment may then be broken to allow the soluble indicator protein to come into contact with a substrate contained within the second compartment. A luminometer may be used to detect the reaction of indicator (e.g., luciferase) with a substrate. Experiments utilizing this method are described herein. In some embodiments, following infection, the contents of the device may be pulled back into the first compartment in order to mix the infected bacteria with the substrate. In further embodiments, the contents may then pushed back into the second compartment such that the indicator signal can be read in the luminometer.

In some embodiments, the sample may be enriched prior to testing by incubation in conditions that encourage growth. In such embodiments, the enrichment period can be 1, 2, 3, 4, 5, 6, 7, or up to 8 hours or longer, depending on the sample type and size.

Thus, in some embodiments, the indicator bacteriophage comprises a detectable indicator moiety, and infection of a single pathogenic cell (e.g., bacterium) can be detected by an amplified signal generated via the indicator moiety. Thus the method may comprise detecting an indicator moiety produced during phage replication, wherein detection of the indicator indicates that the bacterium of interest is present in the sample.

In in some embodiments, the indicator bacteriophage comprises a detectable indicator moiety, and infection of a single pathogenic cell (e.g., bacterium) can be detected by an amplified signal generated via the indicator moiety. Thus the method may comprise detecting an indicator moiety produced during phage replication, wherein detection of the indicator indicates that the bacterium of interest is present in the sample.

As described in more detail herein, the methods and systems of the invention may utilize a range of concentrations of parental indicator bacteriophage to infect bacteria present in the sample. In some embodiments the indicator bacteriophage are added to the sample at a concentration sufficient to rapidly find, bind, and infect target bacteria that are present in very low numbers in the sample, such as a single cell. In some embodiments, the phage concentration can be sufficient to find, bind, and infect the target bacteria in less than one hour. In other embodiments, these events can occur in less than two hours, or less than three hours, following addition of indicator phage to the sample. For example, in certain embodiments, the bacteriophage concentration for the incubating step is greater than $1\times10^5$ PFU/mL, greater than $1\times10^6$ PFU/mL, or greater than $1\times10^7$ PFU/mL.

Methods of the invention may comprise various other steps to increase sensitivity. For example, as discussed in more detail herein, the method may comprise a step for capturing and washing the captured and bound bacterium, to remove excess recombinant bacteriophage and increase the signal to noise ratio. In some embodiments, positive detection of the indicator moiety requires that the ratio of signal to background generated by detecting the indicator moiety is at least 2.0 or at least 2.5.

FIGS. 2-10 demonstrate data and plots of those data from exemplary embodiments of recombinant bacteriophage assays.

Figure 3B:
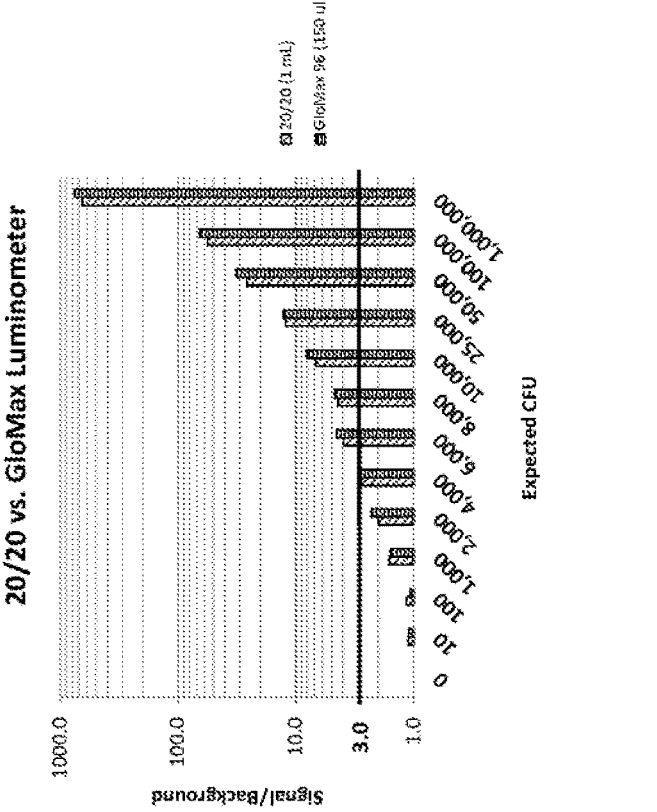
FIGS. 3A and 3B are plots generated from the data shown in Table 1.
Figure 3A:
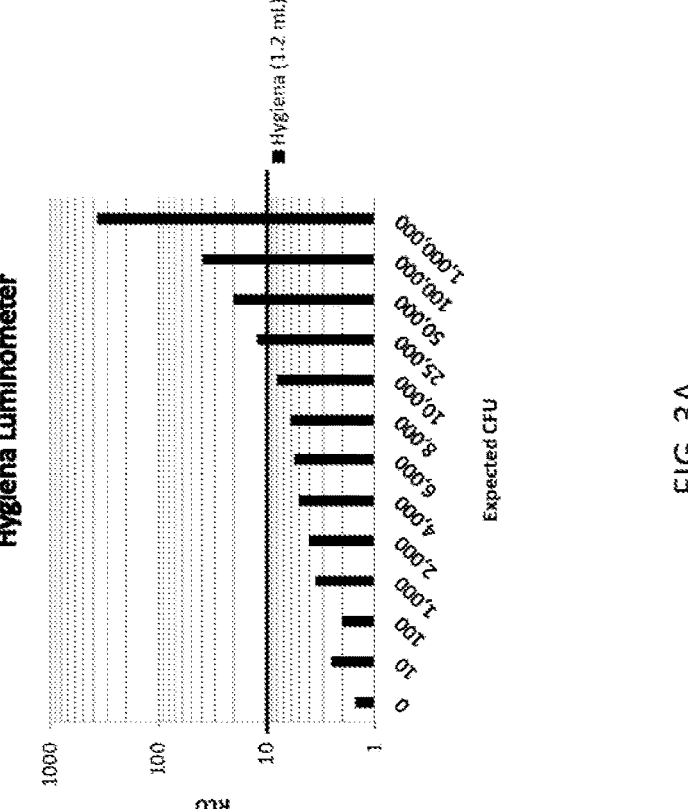

FIGS. 2, 3A, and 3B relate to detection of *L. monocytogenes*. FIG. 2 shows data from detection of *L. monocytogenes* culture using one embodiment of a self-contained apparatus with a swab as a solid support. The signals corresponding to the presence of the bacteria was detected by Hygiena, GloMax, and GloMax 20/20 luminometers. Table 1 shows results from log phase culture and Table 2 shows results from overnight culture.

FIGS. 3A and 3B are plots generated from the data shown in Table 1. FIG. 3A shows measurements of signals detected using Hygiena. Swabs were inoculated with log phase cells at the indicated CFU level. Sample was immediately infected with *Listeria* phage cocktail for 4 hours. Substrate was added and samples were read on the Hygiena Luminometer. A signal of >10 RLU is considered positive. With this method, approximately 25,000 CFU is required to generate a positive result.

FIG. 3B shows the measurements of signals detected using GloMax 20/20 and GloMax (a.k.a., GloMax 96) luminometers. Swabs were inoculated with log phase cells at the indicated CFU level. Sample was immediately infected with *Listeria* phage cocktail for 4 hours. Substrate was added and samples were read on either the GloMax 20/20 (1 mL of sample) or GloMax (150 µl of sample) Luminometers. A signal/background ratio of >3.0 is considered positive. With this method, approximately 5,000 CFU is required to generate a positive result.

FIGS. 4-8 relate to embodiments demonstrating detection of *Salmonella*. FIG. 4 shows the results of detecting *Salmonella* in ground turkey that has been inoculated with *Salmonella*. Table 3 shows uninoculated control sample, and Table 4 shows inoculated turkey sample. The tests were repeated with varying incubation and infection time.

Figures 5A, 5B:
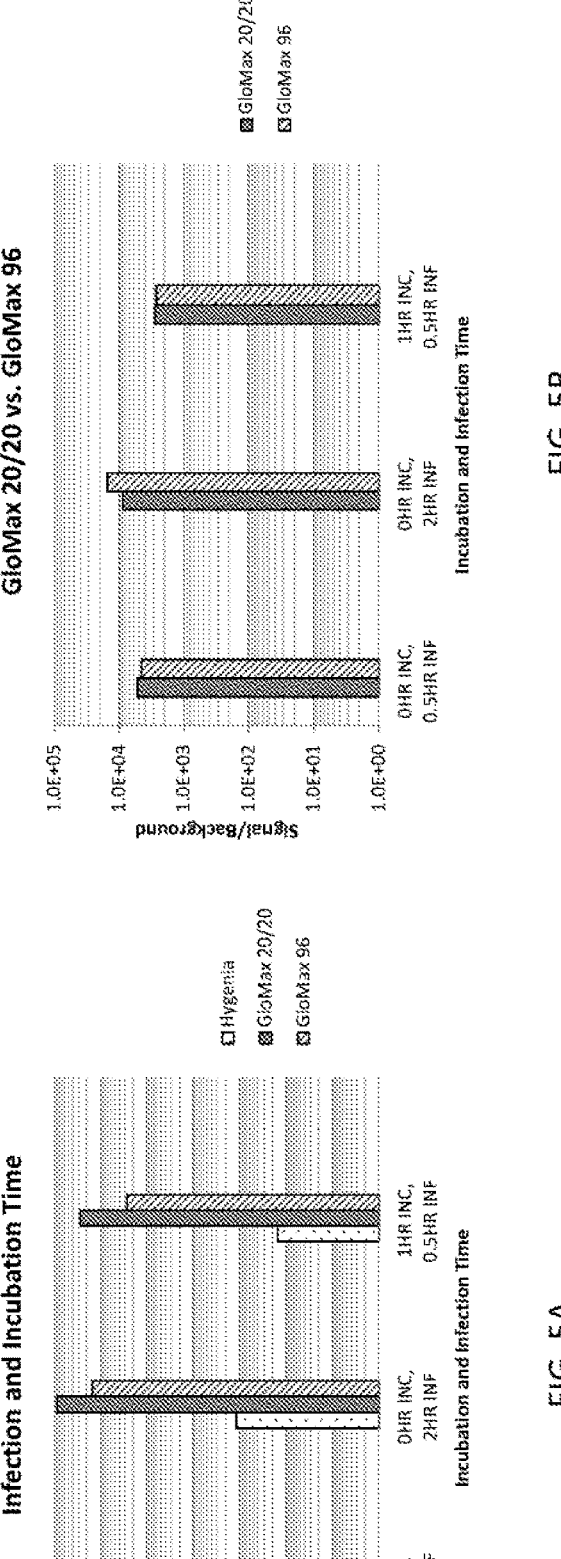
FIG. 5A and FIG. 5B are plots generated from the data in FIG. 4.

FIG. 5A and FIG. 5B are plots generated from the data in FIG. 4. FIG. 6A shows that *Salmonella*-inoculated turkey samples were detected as positive with every incubation and infection time tested. The turkey sample was grown for 24 hours at 41° C. after inoculation before testing with the methods disclosed in the application. For relative signal: 0 HR incubation, 2 HR infection >1 HR incubation, 0.5 HR infection >0 HR incubation, 0.5 HR infection. In addition, comparison of RLU signal shows that the GloMax luminometers have a much higher signal that that of the Hygiena luminometer.

FIG. 5B shows that detecting using GloMax 20/20 and GloMax luminometers produced similar signal/background ratios for the same samples. Although the GloMax 20/20 had a greater signal (FIG. 5A), the background was significantly higher than that with the GloMax. Thus when determining the signal/background, the two luminometers perform similarly.

FIG. 6 shows data for detecting *Salmonella* in three turkey samples (samples 21, 24, and 26) that had been inoculated with *Salmonella* before the assays using the self-contained apparatus. The samples were infected for different duration of time as indicated before detection of the signal.

FIGS. 7A-7C are plots generated from the data shown in FIG. 6. FIGS. 7A-7C show results of the experiments in which three inoculated ground turkey samples were enriched for 24 hours and swab samples were taken and assayed. Sample 24 (FIG. 7B) and 26 (FIG. 7C) did not show signal on Hygiena handheld luminometer for samples that had 30 min phage infection, but did for sample that had 2 hour infection. The GloMax 20/20 and GloMax luminometer generated relatively low signals.

FIGS. 8A-8C are plots generated from the data shown in FIG. 6. The plots show both GloMax 20/20 and GloMax were able to detect Sample 21 (FIG. 8A) and 26 (FIG. 8B) as positive with 30 minute infection (signal/background ratio of >3.0 is positive), however Sample 24 (FIG. 8C) required a 2 hour infection to show a positive result. The GloMax 20/20 and GloMax luminometer results were similar.

FIG. 9 shows data for detecting *L. monocytogenes* environmental sponge samples from inoculated surfaces and enriched for 24 hours.

FIG. 10 shows detecting microorganisms in *Salmonella*-inoculated turkey samples using the apparatus. The signals were measured using three different luminometers: GloMax, 3M, and Hygiena.

Recombinant bacteriophage assays retain specificity over time. In numerous embodiments over multiple years of development and utilization of recombinant bacteriophage assays for, e.g., *E. coli, Cronobacter, Salmonella, Listeria* and *S. aureus*, changes in host specificity were not observed. These embodiments include more than 25 recombinant luciferase reporter or indicator bacteriophages. Further, loss or inactivation of the reporter or indicator (e.g., luciferase) gene has not been detected in any recombinant phage as described herein. Recombinant bacteriophages are stored and preserved in multiple aliquots to protect against mishandling. Although bacteriophages are intrinsically stable, titers may decrease to a variable extent over extended storage, e.g., for months or years at 4° C. This is generally believed to be due to loss of DNA from particles; however, active bacteriophage are recovered by plating for plaques to obtain higher titers. Specificity verification is performed with each recombinant bacteriophage preparation by infecting different bacterial strains that are known to be positive and negative.

In some embodiments of methods for testing samples, the use of a large excess of recombinant bacteriophage necessitates separation of any unbound bacteria or other larger components of the sample from the excess of unbound recombinant bacteriophage. This may be accomplished in many different ways generally known by one of ordinary skill in the art. Microorganism cells can be separated through centrifugation, filtration by size, or selective immobilization. In some embodiments, filtration by size is accomplished through filter wells. In other embodiments, magnetic separation can be used for selective immobilization. For example, the sample may be filtered through a 0.45 µm or 0.22 µm membrane, either before or after incubating with the recombinant bacteriophage, to capture the target microorganism (e.g., bacterium) on a solid support. The captured microorganism may then be washed one or more times on the solid support to ensure that only specifically bound recombinant bacteriophage remains. Or a mechanism for specific or non-specific binding can be employed to capture the microorganism on micro-beads or another solid surface. Other formats for separating components of the sample are possible.

A variety of solid supports may be used. In certain embodiments, the solid support may comprise a multi-well plate, a filter, a bead, a lateral flow strip, a filter strip, filter disc, filter paper, or thin films designed for culturing cells (e.g., PetriFilm by 3M). Other solid supports may also be appropriate. For example, in some embodiments the test sample microorganism may be captured by binding to a swab, the surface of a plate, or by filtering the sample through a bacteriological filter (e.g., 0.45 μm pore size spin filter or plate filter). In one embodiment, the microorganism captured on the filter or plate surface is incubated with recombinant bacteriophage and subsequently washed one or more times to remove excess unbound recombinant bacteriophage.

Alternatively, in some embodiments the capturing step may be based on other features of the microorganism of interest, such as size. In embodiments utilizing size-based capture, the solid support may be a spin column filter. In some embodiments, the solid support comprises a 96-well filter plate. Or, the solid support for capture may be a location on an array, or a mobile support, such as a bead.

In some embodiments, the solid support is coated with a cell binding component that binds with high affinity to the microorganism of interest in the sample. This allows the more bacteria binding to the solid support and increase assay sensitivity and specificity.

In an embodiment, where the microorganism of interest is a bacterium, the recombinant bacteriophage may bind to the bacterium via a cell binding domain from the bacteriophage. For example, well-studied phages of *E. coli* include T1, T2, T3, T4, T5, T7, and lambda; other *E. coli* phages available in the ATCC collection, for example, include phiX174, S13, Ox6, MS2, phiV1, fd, PR772, and ZIK1. *Salmonella* phages include SPN1S, 10, epsilon15, SEA1, and P22. *Listeria* phages include LipZ5, P40, vB_LmoM_AG20, P70, and A511. *Staphylococcus* phages include P4W, virus K, Twort, phi11, 187, P68, and phiWMY.

In some embodiments, the sample may be enriched prior to testing by incubation in conditions that encourage growth. In such embodiments, the enrichment period can be 1, 2, 3, 4, 5, 6, 7, or up to 8 hours or longer, depending on the sample type and size.

In other embodiments, the sample may be enriched following capture of the bacterium on a solid support. In such embodiments, the enrichment period can be 1, 2, 3, 4, 5, 6, 7, or up to 8 hours or longer, depending on the sample type and size.

Thus, in some embodiments, the recombinant bacteriophage comprises a detectable indicator moiety, and binding to a single pathogenic cell (e.g., bacterium) can be detected by an amplified signal generated via the indicator moiety. Thus the method may comprise detecting an indicator moiety of the recombinant bacteriophage, wherein detection of the indicator indicates that the bacterium of interest is present in the sample.

In some embodiments of the methods of the invention, the microorganism may be detected without any isolation or purification of the microorganisms from a sample. For example, in certain embodiments, a sample containing one or more microorganisms of interest may be applied directly to an assay container such as a spin column, a microtiter well, or a filter and the assay is conducted in that assay container. That is, microorganisms are captured on a membrane having pore size too small to allow the microorganisms to pass through. Various embodiments of such assays are disclosed herein.

Aliquots of a test sample may be distributed directly into wells of a multi-well plate, recombinant bacteriophage may be added, and after a period of time sufficient for binding, the cells may be captured on a solid surface such as a plate, bead, or a filter substrate, such that excess unbound recombinant bacteriophage can be removed in one or more subsequent washing steps. Then a substrate for the indicator moiety (e.g., luciferase substrate for a luciferase indicator) is added and assayed for detection of the indicator signal. Some embodiments of the method can be performed on filter plates. Some embodiments of the method can be performed with or without concentration of the sample before binding with recombinant bacteriophage.

For example, in many embodiments, multi-well plates are used to conduct the assays. The choice of plates (or any other container in which detecting may be performed) may affect the detecting step. For example, some plates may include a colored or white background, which may affect the detection of light emissions. Generally, white plates have higher sensitivity but also yield a higher background signal. Other colors of plates may generate lower background signal but also have a slightly lower sensitivity. Additionally, background signal can result from the leakage of light from one well to another, adjacent well. Some plates have white wells while the rest of the plate is black, thus, allowing for a high signal inside the well while preventing well-to-well light leakage. This combination of white wells with black plates may decrease background signal. Thus the choice of plate or other assay vessel may influence the sensitivity and background signal for the assay. In some embodiments, detection of the microorganism of interest may be completed without the need for culturing the sample. For example, in certain embodiments the total time required for detection is less than 12.0 hours, 11.0 hours, 10.0 hours, 9.0 hours, 8.0 hours, 7.0 hours, 6.0 hours, 5.0 hours, 4.0 hours, 3.0 hours, 2.5 hours, 2.0 hours, 1.5 hours, 1.0 hour, 45 minutes, or less than 30 minutes. Minimizing time to result is critical in food and environmental testing for pathogens.

In contrast to assays known in the art, the method of the invention can detect individual microorganisms. Thus, in certain embodiments, the method may detect ≤10 cells of the microorganism (i.e., 1, 2, 3, 4, 5, 6, 7, 8, 9, 10 microorganisms) or ≤20, or ≤30, or ≤40, or ≤50, or ≤60, or ≤70, or ≤80, or ≤90, or ≤100, or ≤200, or ≤500, or ≤1000 cells of the microorganism present in a sample. For example, in certain embodiments, the recombinant bacteriophage is highly specific for *S. Aureus, Listeria, Salmonella,* or *E. coli*. In an embodiment, the recombinant bacteriophage can distinguish *S. Aureus, Listeria, Salmonella,* or *E. coli* in the presence of more than 100 other types of bacteria. In an embodiment, the recombinant bacteriophage can distinguish a specific serotype within a species of bacteria (e.g., *E. coli* O157:H7) in the presence of more than 100 other types of bacteria. In certain embodiments, the recombinant bacteriophage can be used to detect a single bacterium of the specific type in the sample. In certain embodiments, the recombinant bacteriophage detects as few as 2, 3, 4, 5, 6, 7, 8, 9, 10, 15, 20, 30, 40, 50, 60, 70, 80, 90, or 100 of the specific bacteria in the sample.

Thus, aspects of the present invention provide methods for detection of microorganisms in a test sample via a reporter or an indicator moiety. In some embodiments, where the microorganism of interest is a bacterium, the indicator moiety may be associated with a recombinant bacteriophage. The indicator moiety may react with a substrate to emit a detectable signal or may emit an intrinsic signal (e.g., fluorescent protein). Fluorescent proteins naturally fluoresce (intrinsic fluorescence or autofluorescence) by emitting energy as a photon when the fluorescent moiety containing electrons absorb a photon. Fluorescent proteins (e.g., GFP) can be expressed as a fusion protein. In some embodiments, the detection sensitivity can reveal the presence of as few as 100, 50, 20, 10, 9, 8, 7, 6, 5, 4, 3, or 2 cells of the microorganism of interest in a test sample. In some embodiments, even a single cell of the microorganism of interest may yield a detectable signal.

The selection of a particular indicator moiety is not critical to the present invention, but the indicator moiety will be capable of generating a detectable signal either by itself, or be instrumentally detectable, or be detectable in conjunction with one or more additional signal producing components, such as an enzyme/substrate signal producing system. A number of recombinant bacteriophages can be formed by varying either the indicator moiety or reporter of the recombinant bacteriophage; it will be appreciated by one skilled in the art that the choice involves consideration of the microorganism to be detected and the desired means of detection.

For example, one or more signal producing components can be reacted with the indicatory moiety to generate a detectable signal. In some embodiments, the indicator can be a bioluminescent compound. If the indicator moiety is an enzyme, then amplification of the detectable signal is obtained by reacting the enzyme with one or more substrates or additional enzymes and substrates to produce a detectable reaction product. In an alternative signal producing system, the indicator can be a fluorescent compound where no enzymatic manipulation of the indicator is required to produce the detectable signal. Fluorescent molecules including, for example, fluorescein and rhodamine and their derivatives and analogs are suitable for use as indicators in such a system. In yet another alternative embodiment, the indicator moiety can be a cofactor, then amplification of the detectable signal is obtained by reacting the cofactor with the enzyme and one or more substrates or additional enzymes and substrates to produces a detectable reaction product. In some embodiments, the detectable signal is colorimetric.

The detectable indicator moiety is a key feature of the recombinant bacteriophage, which can be detected directly or indirectly. The indicator moiety provides a detectable signal by which the binding reaction is monitored providing a qualitative and/or quantitative measure. The relative quantity and location of signal generated by the decorated or signalized microorganisms can serve to indicate the presence and/or quantity of the microorganism. The indicator moiety can also be used to select and isolate decorated or signalized microorganisms, such as by flow sorting or using magnetic separation media.

In some embodiments, the indicator moiety of the recombinant bacteriophage may be detectable directly or after incubation with a substrate. Many different types of detectable biomolecules suitable for use as indicator moieties are known in the art, and many are commercially available. In some embodiments the recombinant bacteriophage comprises an enzyme, which serves as the indicator moiety. In some embodiments, the indicator or reporter of the recombinant bacteriophage encodes a detectable enzyme. The indicator moiety may emit light and/or may be detectable by a color change. Various appropriate enzymes are commercially available, such as alkaline phosphatase (AP), horseradish peroxidase (HRP), green fluorescent protein (GFP), or luciferase (Luc). In some embodiments, these enzymes may serve as the indicator moiety. In some embodiments, Firefly luciferase is the indicator moiety. In some embodiments, *Oplophorus* luciferase is the indicator moiety. In some embodiments, NANOLUC® is the indicator moiety. Other engineered luciferases or other enzymes that generate detectable signals may also be appropriate indicator moieties.

Thus, in some embodiments, the recombinant bacteriophage of the methods, systems or kits is a wild-type bacteriophage genetically modified with the sequence of an indicator protein, such as a fluorescent protein or a luciferase protein.

Bacteriophages are able to infect and lyse specific bacteria.

Detecting the indicator may include detecting emissions of light. In some embodiments, a luminometer may be used to detect the reaction of indicator (e.g., luciferase) with a substrate. The detection of RLU can be achieved with a luminometer, or other machines or devices may also be used. For example, a spectrophotometer, CCD camera, or CMOS camera may detect color changes and other light emissions. Absolute RLU are important for detection, but the signal to background ratio also needs to be high (e.g., >2.0, >2.5, or >3.0) in order for single cells or low numbers of cells to be detected reliably.

In some embodiments, the reaction of indicator moiety (e.g., luciferase) with substrate may continue for 30 minutes or more, and detection at various time points may be desirable for optimizing sensitivity. For example luminometer readings may be taken initially and at 3-, or 5-, or 10-, or 15-minute intervals until the reaction is completed.

Thus in some embodiments utilizing recombinant bacteriophage, the invention comprises a method for detecting a microorganism of interest comprising the steps of capturing at least one sample bacterium; incubating the at least one bacterium with a plurality of recombinant bacteriophage; allowing time for binding to target microorganism in the sample; and detecting the indicator moiety, wherein detection of the indicator moiety demonstrates that the bacterium is present in the sample.

For example, in some embodiments the test sample bacterium may be captured by binding to the surface of a plate, or by filtering the sample through a bacteriological filter (e.g., 0.45 μm pore size spin filter or plate filter). In an embodiment, the recombinant bacteriophage is added in a minimal or modest volume to the captured sample directly on the filter. In an embodiment, the microorganism captured on the filter or plate surface is subsequently washed one or more times to remove excess unbound recombinant bacteriophage.

In some embodiments, aliquots of a test sample comprising bacteria may be applied to a spin column and after incubation with a recombinant bacteriophage and washing to remove any excess bacteriophage, the amount of indicator detected will be proportional to the amount of target bacteria present in the sample.

The indicator (e.g., luciferase) bound to the bacteria may then be measured and quantified. In an embodiment, the solution is spun through the filter, and the filtrate collected for assay in a new receptacle (e.g., in a luminometer) following addition of a substrate for the indicator enzyme (e.g., luciferase substrate). Alternatively, the indicator signal may be measured directly on the filter.

In an embodiment, the microorganism is a bacterium and the recombinant bacteriophage includes an indicator moiety derived from a bacteriophage. In an embodiment, the indicator moiety is luciferase. Thus, in an alternate embodiment, the indicator substrate (e.g., luciferase substrate) may be incubated with the portion of the sample that remains on a filter or bound to a plate surface. Accordingly, in some embodiments the solid support is a 96-well filter plate (or regular 96-well plate), and the substrate reaction may be detected by placing the plate directly in the luminometer.

For example, in an embodiment, the invention may comprise a method for detecting a pathogenic bacterium of interest comprising the steps of: binding cells captured on a 96-well filter plate with a plurality of recombinant bacteriophage; washing excess recombinant bacteriophage away; and detecting the indicator (e.g., luciferase) by adding substrate and measuring enzyme activity directly in the 96-well plate, wherein detection of enzyme activity indicates that the bacterium of interest is present in the sample.

In another embodiment, the invention may comprise a method for detecting a microorganism of interest, such as *S. aureus*, comprising the steps of: binding cells in liquid solution or suspension in a 96-well plate with a plurality of recombinant bacteriophage; washing unbound recombinant bacteriophage away from cells having bound recombinant bacteriophage; and detecting the indicator (e.g., luciferase) by adding substrate and measuring enzyme activity directly in the 96-well plate, wherein detection of enzyme activity indicates that the microorganism of interest, such as *S. aureus*, is present in the sample. In some embodiments, the microorganism of interest may be captured on a solid support such as on beads or a filter. This capturing can occur either before or after incubation with the recombinant bacteriophage. In some embodiments no capturing step is necessary.

In some embodiments, the liquid solution or suspension may be a consumable test sample, such as a vegetable wash. In some embodiments, the liquid solution or suspension may be vegetable wash fortified with concentrated LB Broth, Tryptic/Tryptone Soy Broth, Peptone Water, or Nutrient Broth. In some embodiments, the liquid solution or suspension may be bacteria diluted in LB Broth.

In some embodiments, target microorganism cells need to be intact for proper detection. That is, the cells need not be viable, but the cell wall must be structurally intact. Thus it is desirable to minimize lysis of the bacterium before the detection step.

In some embodiments, an initial concentration step for the sample is useful. That is, any microorganisms or other relatively large substances in the sample are concentrated to remove excess liquid. However it is possible to perform the assay without an initial concentration step. Some embodiments do include an initial concentration step, and in some embodiments this concentration step allows a shorter enrichment incubation time. In other embodiments, no enrichment period is necessary.

Some embodiments of testing methods may further include confirmatory assays. A variety of assays are known in the art for confirming an initial result, usually at a later point in time. For example, the samples can be cultured (e.g., CHROMAGAR®/DYNABEADS® assay), PCR can be utilized to confirm the presence of the microbial DNA, or other confirmatory assays can be used to confirm the initial result.

Embodiments of food safety assays include sample preparation steps. Some embodiments can include enrichment time. For example, enrichment for 1, 2, 3, 4, 5, 6, 7, or 8 hours may be needed, depending on sample type and size.

Following these sample preparation steps, binding with a high concentration of recombinant bacteriophage that comprises a reporter or indicator can be performed in a variety of assay formats, such as that shown in FIG. 1.

Embodiments of food assays can detect a single pathogenic bacterium in sample sizes corresponding to industry standards, with a reduction in time-to-results of at least 20%, or at least 30%, or at least 40% or at least 50% or at least 60% depending on the sample type and size.

Thus, some embodiments of the present invention solve a need by using recombinant bacteriophage methods for amplifying a detectable signal indicating the presence of bacteria. In certain embodiments as little as a single bacterium is detected. The principles applied herein can be applied to the detection of a variety of microorganisms. In this way, embodiments of the present invention can achieve tremendous signal amplification from even a single cell of the microorganism of interest.

Aspects of the present invention utilize the high specificity of binding components that can bind to particular microorganisms, such as the recognition and binding component of infectious agents, as a means to detect and/or quantify the specific microorganism in a sample. In some embodiments, the present invention takes advantage of the specificity of bacteriophages.

Some embodiments of the invention disclosed and described herein utilize the discovery that a single microorganism is capable of generating a large amount of indicator following infection with recombinant bacteriophage. This principle allows amplification of indicator signal from one or a few cells based on specific recognition of the microorganism. For example, by exposing even a single cell of a bacterium to a plurality of recombinant bacteriophage, the indicator signal is amplified such that a single bacterium is detectable.

The unprecedented speed and sensitivity of detecting a microorganism with recombinant bacteriophages are unexpected results. In some embodiments, the methods of the invention require less than 12, 11, 10, 9, 8, 7, 6, 5, 4, 3, or 2 hours for detection of a microorganism of interest. These are shorter timeframes than were previously thought possible. In some embodiments, the methods can detect as few as 100, 50, 20, 10, 9, 8, 7, 6, 5, 4, 3, or 2 cells of the bacterium of interest. In some embodiments, even a single cell of the bacterium is detectable. In additional embodiments, the invention comprises systems (e.g., computer systems, automated systems or kits) comprising components for performing the methods disclosed herein, and/or using the recombinant bacteriophages described herein.

Existing protocols for detection of pathogenic bacteria in foods are complicated, expensive, slow, labor-intensive and prone for false positives. Moreover, phage-based detection methods include the added complication and regulatory implications of infectious reagents. Detection with a recombinant bacteriophage specific for a given pathogen offers an effective, fast and simple testing alternative.

Infectious agents can be highly specific to a particular type of organism. For example, a bacteriophage may be specific to a particular genus of a bacterium, such as *Listeria*. For example, the A511 bacteriophage is specific for the genus *Listeria*. Or a bacteriophage may be specific to a particular species of bacterium, such as *E. coli*. For some types of bacteria, bacteriophages may even recognize particular subtypes of that organism with high specificity. For example, the CBA120 bacteriophage is highly specific for *E. coli* O157:H7 and the φYeO3-12 bacteriophage is highly specific for *Y. enterocolitica* serotype O:3.

In some embodiments of the recombinant bacteriophage described herein, the recombinant bacteriophage can be derived from T7, T4, T4-like, ViI, ViI-like, AR1, A511, A118, A006, A500, PSA, P35, P40, B025, B054, A97, phiSM101, phi3626, CBA120, SPN1S, 10, epsilon15, P22, LipZ5, P40, vB_LmoM_AG20, P70, A511, P4W, K, Twort, or SA97. A recombinant bacteriophage also includes an indicator moiety, such as a fluorescent moiety, a fluorescent protein, a bioluminescent protein, or an enzyme, that allows the recombinant bacteriophage to generate a signal. In a recombinant bacteriophage, various types of reporters can be inserted into the bacteriophage genome, to serve as an indicator moiety. In some embodiments, the recombinant bacteriophage comprises an enzyme, such as a luciferase, which is only detectable upon addition of an appropriate substrate. For example, luciferase, alkaline phosphatase, and other reporter enzymes react with an appropriate substrate to provide a detectable signal. Some embodiments of a recombinant bacteriophage comprise a wild-type luciferase or an engineered luciferase, such as NANOLUC®. Other embodiments include a fluorescent protein or another reporter protein.

In alternate embodiments, bacteriophages, phages, myco-bacteriophages (such as for TB and paraTB), mycophages (such as for fungi), mycoplasma phages, and any other virus that can invade living bacteria, fungi, mycoplasma, protozoa, yeasts, and other microscopic living organisms can be studied or copied to target a microorganism of interest. For example, well-studied phages of *E. coli* include T1, T2, T3, T4, T5, T7, and lambda; other *E. coli* phages available in the ATCC collection, for example, include phiX174, S13, Ox6, MS2, phiV1, fd, PR772, and ZIK1. *Salmonella* phages include SPN1S, 10, epsilon15, SEA1, and P22. *Listeria* phages include LipZ5, P40, vB_LmoM_AG20, P70, and A511. *Staphylococcus* phages include P4W, virus K, Twort, phi 11, 187, P68, and phiWMY.

Some embodiments of the invention utilize the specificity of binding of a recombinant bacteriophage for rapid and sensitive targeting to bind and facilitate detection of a bacterium of interest.

In some embodiments, a recombinant bacteriophage is derived from a bacteriophage specific for a target bacterium of interest, such as from T7, T4 or another similar phage. A recombinant bacteriophage may also be derived from T4-like, T7-like, ViI, ViI-like, AR1, A511, A118, A006, A500, PSA, P35, P40, B025, B054, A97, phiSM101, phi3626, CBA120, SPN1S, 10, epsilon15, P22, LipZ5, P40, vB_LmoM_AG20, P70, A511, P4W, K, Twort, or SA97.

In some embodiments, a small indicator gene product may be desirable. OpLuc and NANOLUC® proteins are only about 20 kDa (approximately 500-600 bp to encode), while FLuc is about 62 kDa and requires approximately 1,700 bp to encode. For comparison, the genome of T7 is around 40 kbp, while the T4 genome is about 170 kbp.

Moreover, the indicator should generate a high signal to background ratio and should be readily detectable in a timely manner. Promega's NANOLUC® is a modified *Oplophorus gracilirostris* (deep sea shrimp) luciferase. In some embodiments, NANOLUC® combined with Promega's NANO-GLO®, an imidazopyrazinone substrate (furimazine), can provide a robust signal with low background.

In some recombinant bacteriophage embodiments, an indicator moiety can be any of a variety of biomolecules. The indicator can be a detectable product or an enzyme that produces a detectable product or a cofactor for an enzyme that produces a detectable product. In some embodiments, the indicator moiety of a recombinant bacteriophage is a reporter, such as a detectable enzyme. The indicator gene product may generate light and/or may be detectable by a color change. Various appropriate enzymes are commercially available, such as alkaline phosphatase (AP), horseradish peroxidase (HRP), or luciferase (Luc). For example, in one embodiment the indicator is a luciferase enzyme. Various types of luciferase may be used. In alternate embodiments, and as described in more detail herein, the luciferase is one of *Oplophorus* luciferase, Firefly luciferase, Lucia luciferase, Renilla luciferase, or an engineered luciferase. In some embodiments, the luciferase is derived from *Oplophorus*. In some embodiments, the indicator is a genetically modified luciferase, such as NANOLUC®. Other engineered luciferases or other enzymes that generate detectable signals may also be appropriate indicator moieties. In some embodiments, these enzymes may serve as the indicator moiety.

Compositions of the invention may comprise one or more recombinant bacteriophages derived from one or more wild-type infectious agents (e.g., bacteriophages) and one or more indicator moieties. In some embodiments, compositions can include cocktails of different recombinant bacteriophages that may generate the same or different indicator signals. That is, a composition for detecting a microorganism can include all the same or different recombinant bacteriophages.

Assays previously described utilize recombinant bacteriophage which recognize and bind to specific bacteria can be employed. The recombinant bacteriophage assays can be performed in a traditional laboratory setting or in a device, such as for example an apparatus as described further herein.
Recombinant Bacteriophage As described in more detail herein, the apparatus, methods, systems and kits of the invention comprise recombinant bacteriophage for use in detection of microorganisms of interest. The recombinant bacteriophage are comprised in the first compartment of the apparatus disclosed above. In some embodiments, the invention may include a composition comprising a recombinant bacteriophage having an indicator gene incorporated into the genome of the bacteriophage. In some embodiments, the indicator gene is operably linked to a promoter that is not a native promoter of the bacteriophage. In some embodiments, the indicator gene is operably linked to a native promoter of the bacteriophage. The recombinant bacteriophage comprising the indicator or reporter gene are also referred to as indicator bacteriophage in this disclosure.

A recombinant bacteriophage can include a reporter or indicator gene. In certain embodiments of the bacteriophage, the indicator gene does not encode a fusion protein. For example, in certain embodiments, expression of the indicator gene during bacteriophage replication following infection of a host bacterium results in a soluble indicator protein product. In certain embodiments, the indicator gene may be inserted into a late gene region of the bacteriophage. Late genes are generally expressed at higher levels than other phage genes, as they code for structural proteins. The late gene region may be a class III gene region and may include a gene for a major capsid protein.

Some embodiments include designing (and optionally preparing) a sequence for homologous recombination downstream of the major capsid protein gene. Other embodiments include designing (and optionally preparing) a sequence for homologous recombination upstream of the major capsid protein gene. In some embodiments, the sequence comprises a codon-optimized reporter gene preceded by an untranslated region. The untranslated region may include a phage late gene promoter and ribosomal entry site.

In some embodiments, an indicator bacteriophage is derived from A511, P100, *Listeria* phage LMTA-94, LMA4, LMA8, T7, T4 or another similar phage. An indicator bacteriophage may also be derived from P100virus, T4-like, T7-like, ViI, ViI-like, *Cronobacter-*, *Salmonella-*, *Listeria-* or *Staphylococcus*-specific bacteriophage, or another bacteriophage having a genome with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to T7, T7-like, T4, T4-like, P100virus, *Cronobacter-*, *Salmonella-*, *Listeria-* or *Staphylococcus*-specific bacteriophage, ViI, or ViI-like (or Vi1 virus-like, per GenBank/NCBI) bacteriophages. In some embodiments, the indicator phage is derived from a bacteriophage that is highly specific for a particular pathogenic microorganism. The genetic modifications may avoid deletions of wild-type genes and thus the modified phage may remain more similar to the wild-type bacteriophage than many commercially available phage. Environmentally derived bacteriophage may be more specific for bacteria that are found in the environment and as such, genetically distinct from phage available commercially.

Moreover, phage genes thought to be nonessential may have unrecognized function. For example, an apparently nonessential gene may have an important function in elevating burst size such as subtle cutting, fitting, or trimming functions in assembly. Therefore, deleting genes to insert an indicator may be detrimental. Most phages can package a DNA that is a few percent larger than their natural genome. With this consideration, a smaller indicator gene may be a more appropriate choice for modifying a bacteriophage, especially one with a smaller genome. OpLuc and NANO-LUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp, and the genome of *Cronobacter-*, *Salmonella-*, or *Staphylococcus*-specific bacteriophage is about 157 kbp. Moreover, the reporter gene should not be expressed endogenously by the bacteria (i.e., is not part of the bacterial genome), should generate a high signal to background ratio, and should be readily detectable in a timely manner. Promega's NANOLUC® is a modified *Oplophorus gracilirostris* (deep sea shrimp) luciferase. In some embodiments, NANOLUC® combined with Promega's NANO-GLO®, an imidazopyrazinone substrate (furimazine), can provide a robust signal with low background.

In some indicator phage embodiments, the indicator gene can be inserted into an untranslated region to avoid disruption of functional genes, leaving wild-type phage genes intact, which may lead to greater fitness when infecting non-laboratory strains of bacteria. Additionally, including stop codons in all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various types of luciferase may be used. In alternate embodiments, and as described in more detail herein, the luciferase is one of *Oplophorus* luciferase, Firefly luciferase, Lucia luciferase, Renilla luciferase, or an engineered luciferase. In some embodiments, the luciferase gene is derived from *Oplophorus*. In some embodiments, the indicator gene is a genetically modified luciferase gene, such as NANOLUC®.

Thus, in some embodiments, the present invention comprises a genetically modified bacteriophage comprising a non-bacteriophage indicator gene in the late (class III) gene region. In some embodiments, the non-native indicator gene is under the control of a late promoter. Using a viral late gene promoter insures the reporter gene (e.g., luciferase) is not only expressed at high levels, like viral capsid proteins, but also does not shut down like endogenous bacterial genes or even early viral genes.

In some embodiments, the late promoter is a P100virus, T4-, T7-, or ViI-like promoter, or another phage promoter similar to that found in the selected wild-type phage, i.e., without genetic modification. The late gene region may be a class III gene region, and the bacteriophage may be derived from T7, T4, T4-like, ViI, ViI-like, *Cronobacter-*, *Salmonella-*, *Staphylococcus-*, *Listeria-* or *S. aureus*-specific bacteriophage, or another natural bacteriophage having a genome with at least 70, 75, 80, 85, 90 or 95% homology to T7, T4, T4-like, ViI, ViI-like, or *Cronobacter-*, *Salmonella-*, *Staphylococcus-*, *Listeria-* or *S. aureus*-specific bacteriophage.

Genetic modifications to bacteriophages may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. In some embodiments, the non-native indicator gene is not part of a fusion protein. That is, in some embodiments, a genetic modification may be configured such that the indicator protein product does not comprise polypeptides of the wild-type bacteriophage. In some embodiments, the indicator protein product is soluble. In some embodiments, the invention comprises a method for detecting a bacterium of interest comprising the step of incubating a test sample with such a recombinant bacteriophage.

In some embodiments, expression of the indicator gene in progeny bacteriophage following infection of host bacteria results in a free, soluble protein product. In some embodiments, the non-native indicator gene is not contiguous with a gene encoding a structural phage protein and therefore does not yield a fusion protein. Unlike systems that employ a fusion of a detection moiety to the capsid protein (i.e., a fusion protein), some embodiments of the present invention express a soluble indicator or reporter (e.g., soluble luciferase). In some embodiments, the indicator or reporter is ideally free of the bacteriophage structure. That is, the indicator or reporter is not attached to the phage structure. As such, the gene for the indicator or reporter is not fused with other genes in the recombinant phage genome. This may greatly increase the sensitivity of the assay (down to a single bacterium), and simplifies the assay, allowing the assay to be completed in less than an hour for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate.

Moreover, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the detection moiety (e.g., luciferase) than can fit on the bacteriophage. Additionally, large fusion proteins, such as a capsid-luciferase fusion, may inhibit assembly of the bacteriophage particle, thus yielding fewer bacteriophage progeny. Thus a soluble, non-fusion indicator gene product may be preferable.

In some embodiments, the indicator phage encodes a reporter, such as a detectable enzyme. The indicator gene product may generate light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, *Oplophorus* luciferase is the indicator moiety. In some embodiments, NANO-LUC® is the indicator moiety. Other engineered luciferases or other enzymes that generate detectable signals may also be appropriate indicator moieties.

In some embodiments, the use of a soluble detection moiety eliminates the need to remove contaminating parental phage from the lysate of the infected sample cells. With a fusion protein system, any bacteriophage used to infect sample cells would have the detection moiety attached, and would be indistinguishable from the daughter bacteriophage also containing the detection moiety. As detection of sample bacteria relies on the detection of a newly created (de novo synthesized) detection moiety, using fusion constructs requires additional steps to separate old (parental) moieties from newly created (daughter bacteriophage) moieties. This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by streptavidin-coated sepharose beads). However, even with all these attempts at removal, parental phage can remain when a high concentration of parental phage is used to assure infection of a low number of sample cells, creating background signal that may obscure detection of signal from infected cell progeny phage.

By contrast, with the soluble detection moiety expressed in some embodiments of the present invention, purification of the parental phage from the final lysate is unnecessary, as the parental phage do not have any detection moiety attached. Thus any detection moiety present after infection must have been created de novo, indicating the presence of an infected bacterium or bacteria. To take advantage of this benefit, the production and preparation of parental phage may include purification of the phage from any free detection moiety produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). Cesium chloride isopycnic ultracentrifugation can be employed as part of the preparation of recombinant phage of the invention, to separate parental phage particles from contaminating luciferase protein produced upon propagation of the phage in the bacterial host. In this way, the parental recombinant bacteriophage of the invention is substantially free of any luciferase generated during production in the bacteria. Removal of residual luciferase present in the phage stock can substantially reduce background signal observed when the recombinant bacteriophage are incubated with a test sample.

In some embodiments of modified bacteriophage, the late promoter (class III promoter, e.g., from *Listeria*-specific phage, T7, T4, or ViI) has high affinity for RNA polymerase of the same bacteriophage that transcribes genes for structural proteins assembled into the bacteriophage particle. These proteins are the most abundant proteins made by the phage, as each bacteriophage particle comprises dozens or hundreds of copies of these molecules. The use of a viral late promoter can ensure optimally high level of expression of the luciferase detection moiety. The use of a late viral promoter derived from, specific to, or active under the original wild-type bacteriophage the indicator phage is derived from (e.g., a *Listeria*-specific phage, T4, T7, or ViI late promoter with a T4-, T7-, or ViI-based system) can further ensure optimal expression of the detection moiety. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator moiety, using a placement in the genome that does not limit expression to the number of subunits of a phage structural component.

Compositions of the invention may comprise one or more wild-type or genetically modified bacteriophages (e.g., bacteriophages) and one or more indicator genes. In some embodiments, compositions can include cocktails of different indicator phages that may encode and express the same or different indicator proteins. In some embodiments, the cocktail of bacteriophage comprises at least two different types of recombinant bacteriophages.

Devices or Apparatus for Detecting Microorganisms

Embodiments of the invention are directed to methods of detecting microorganisms of interest using a self-contained apparatus. In some embodiments, the apparatus comprises a solid support, which can be used for collecting a sample comprising the microorganisms of interest. In some embodiments, an apparatus according to the invention comprises a tube with separate compartments, either arranged sequentially or in branching configuration (e.g., "ears" on a tube). The apparatus may comprise a number of compartments which can be configured for varied mixing of reagents and timing of method steps. In some embodiments, the apparatus comprises at least two compartments. In some embodiments, the uppermost or superior compartment of the tube contains recombinant bacteriophage, and the substrate compartment is below the bacteriophage compartment. In some embodiments, the tube contains growth media.

In some embodiments, the apparatus comprises at least two compartments, including a first compartment comprising recombinant bacteriophage having a genetic construct inserted into a bacteriophage genome, wherein the construct comprises a promoter and a reporter (indicator) gene; an inlet port into the first compartment for adding at least a portion of a test sample to the recombinant bacteriophage; and a second compartment comprising a substrate or developer, wherein the substrate or developer allows detection of the reporter (indicator) gene. In some embodiments the In one embodiment, a first compartment contains recombinant bacteriophage, and a second compartment contains substrate or developer reagent. In some such embodiments both reagents are mixed with a sample at the same time. In other embodiments, a sample is initially added to the first compartment to initiate infection. After a period of time, a conduit to the second compartment is opened to allow addition and mixing of the substrate or developer reagent into the infected sample.

In an alternative embodiment, the first compartment contains lyophilized infectious agent (e.g., lyophilized recombinant bacteriophage) and a second compartment contains substrate or developer reagent. In some such embodiments both reagents are mixed with a sample (optionally wherein microorganisms from the sample are captured on a solid support) at the same time. In other embodiments, a sample is initially added to the first compartment. After a period of time, a conduit to the second compartment is opened to allow addition and mixing of the substrate or developer reagent into the infected sample.

In some embodiments, a seal separates adjacent compartments, the user breaks the seal(s), both substrate and phage encounter the swab at the same time. As luciferase is produced and reacts with the substrate to produce a detectable signal.

In some embodiments, the substrate compartment may be positioned between a media compartment and a recombinant bacteriophage compartment. In other embodiments, the device does not comprise a media compartment and the device is free of media. When a user breaks the seal to apply a reagent to a sample that is captured on the solid support, both reagents can be applied at the same time.

In alternative embodiments, the substrate compartment may be positioned between a media compartment and a recombinant bacteriophage compartment. In other embodiments, the device does not comprise a media compartment and the device is free of media. When a user breaks the seal to apply a reagent to a sample that is captured on the solid support, both reagents can be applied at the same time.

In some embodiments, a solid support is added to a tube where the substrate or developer is at the bottom of the tube; the solid support is pushed into the bottom to begin the reaction between the enzyme and substrate or other reporter and paired reagent. The solid support may be attached to a shaft for ease of handling.

In some embodiments, the solid support comprises a bead coated with a molecule that specifically captures the microorganism of interest (e.g., an antibody or a cell-binding protein). In other embodiments, the solid support comprises a swab or another non-specific capture mechanism.

Alternatively, in any of the embodiments described herein, the device is free of media.

The following figures provide illustrative examples of embodiments of the invention.

In one embodiment, the present disclosure provides a self-contained microorganism detection apparatus system. FIGS. 11A, 11B, and 11C show an embodiment of an apparatus 100. The apparatus comprises a solid support 16 and a container comprising three compartments. Each of the compartments is separated by a snap action seal. The first compartment 10 contains phage, the second compartment 12 contains substrate, and the third compartment 14 contains media. This apparatus allows the phage and substrate to be incubated with the sample at the same time. In some embodiments, the device is free of media (FIG. 11C).

FIGS. 12A, 12B, and 12C show a second embodiment of an apparatus 200. The apparatus comprises a solid support 26 and a container comprising three compartments. Each of the compartments is separated by a snap action seal. The first compartment 20 contains phage, the second compartment 22 contains media, and the third compartment 24 contains substrate. In embodiments, using the apparatus depicted in FIG. 12A, the sample is first incubated with the phage, prior to incubation with the substrate. In further embodiments using the apparatus depicted in FIG. 12B, the solid support is soaked with media prior to collection of the sample. In some embodiments, the device is free of media (FIG. 12C).

FIGS. 13A, 13B, and 13C depict a third embodiment of an apparatus 300. The apparatus comprises a solid support 36 and a container comprising three compartments. Each of the compartments is separated by a snap action seal. The first compartment 30 contains media, the second compartment 32 contains phage, and the third compartment 34 contains substrate. In embodiments, using the apparatus depicted in FIG. 13A, the sample is first incubated with the phage, prior to incubation with the substrate. In further embodiments using the apparatus depicted in FIG. 13B, the solid support is dry prior to collection of the sample. In some embodiments, the device is free of media (FIG. 13C).

FIGS. 14A, 14B, 14C show a fourth embodiment of an apparatus 400. The apparatus comprises a solid support 46 and a container comprising three compartments. Each of the compartments is separated by a snap action seal. The first compartment 40 contains media, the second compartment 42 contains phage, and the third compartment 46 contains substrate. The apparatus has a stop-lock mechanism for phased mixing of reagents. In embodiments, using the apparatus depicted in FIG. 14A, the sample is first incubated with the phage, prior to incubation with the substrate. In further embodiments using the apparatus depicted in FIG. 14B, the solid support is soaked with media prior to collection of the sample. In some embodiments, the device is free of media (FIG. 14C).

FIGS. 15A, 15B, and 15C depict a fifth embodiment of an apparatus 500. The apparatus comprises a solid support 56 and a container comprising three compartments. Each of the compartments is separated by a snap action seal. The first compartment 50 contains media, the second compartment 52 contains phage, and the third compartment 54 contains substrate. The apparatus has a stop-lock mechanism for phased mixing of reagents. In embodiments, using the apparatus depicted in FIG. 15A, the sample is first incubated with the phage, prior to incubation with the substrate. In further embodiments using the apparatus depicted in FIG. 15B, the solid support is dry prior to collection of the sample. In some embodiments, the device is free of media (FIG. 15C).

FIG. 16 depicts a sixth embodiment of an apparatus 600. The apparatus comprises a solid support 64 and a container comprising two compartments. Each of the compartments is separated by a snap action seal. The first compartment 60 contains phage and the second compartment 62 contains substrate. In embodiments, using the apparatus depicted in FIG. 16, the sample is first incubated with the phage, prior to incubation with the substrate.

FIG. 17 depicts an embodiment of a method for detecting microorganisms comprising (i) enriching a sample overnight, (ii) using a solid support from a self-contained apparatus to collect the sample that has been enriched overnight, (iii) infecting the sample with phage contained within a compartment of the self-contained apparatus, and (iv)

detecting the presence of microorganisms by reading/detecting the signal produced by the infection step.

In some embodiments, compartments contained in projections or branches from the central tube allow mixing of reagents from more than 2 directions, e.g., in the form of "ears." For example, two squeeze bulbs could be used to add media and then phage sequentially or simultaneously to the main compartment, or to add other reagents. Various arrangements of other compartments with respect to a central compartment allows for addition and mixing of different reagents into the larger adjacent compartment.

Methods of Using the Apparatus for Detecting Microorganisms

As noted herein, in certain embodiments, the invention may include methods of detecting the microorganism, the method comprising contacting the sample with a solid support such that the microorganisms are captured on the solid support, contacting the recombinant bacteriophage from the first compartment with the microorganisms captured on the solid support by e.g., breaking a snap action seal of the first compartment. During and/or after the infection, the bacteriophage express the indicator gene to produce an indicator, which can be detected by various detection devices. In some embodiments, the detection of the indicator may require adding a substrate, which reacts with the indicator to produce a detectable signal. The presence of the signals indicate the presence of the microorganisms in the sample.

In an alternative embodiment, the invention may include methods of detecting the microorganism, the method comprising contacting the sample with a solid support such that the microorganisms are captured on the solid support, contacting the recombinant bacteriophage from the first compartment with the microorganisms captured on the solid support by e.g., breaking a snap action seal of the first compartment. The indicator moiety of the recombinant bacteriophage can be detected by various detection devices. In some embodiments, the detection of the indicator may require adding a substrate, which reacts with the indicator to produce a detectable signal. The presence of the signals indicate the presence of the microorganisms in the sample.

Sampling

In some embodiments, samples may be used directly in the detection methods of the present invention, without preparation, concentration, or dilution. For example, liquid samples, including but not limited to, milk and juices, may be assayed directly. In other embodiments, samples may be diluted or suspended in solution, which may include, but is not limited to, a buffered solution or a bacterial culture medium. A sample that is a solid or semi-solid may be suspended in a liquid by mincing, mixing or macerating the solid in the liquid. In some embodiments, a sample should be maintained within a pH range that promotes phage attachment to the host bacterial cell. In some embodiments, the preferred pH range may be one suitable for bacteriophage attached to a bacterial cell. A sample should also contain the appropriate concentrations of divalent and monovalent cations, including but not limited to Na+, Mg2+, and K+.

Preferably throughout detection assays, the sample is maintained at a temperature that maintains the viability of any pathogen cell present in the sample. During steps in which bacteriophage, are attaching to bacterial cells, it is preferable to maintain the sample at a temperature that facilitates bacteriophage activity. Such temperatures are at least about 25° C. and no greater than about 45° C. In some embodiments, the samples are maintained at about 37° C. In some embodiments the samples are subjected to gentle mixing or shaking during bacteriophage binding or attachment.

Assays may include various appropriate control samples. For example, control samples, e.g., food samples, without bacteria may be assayed as controls for background signal levels.

Sampling can be performed using a variety of ways. In some embodiments, the samples, e.g., food samples are first liquefied and the solid support, e.g., the solid support or bead, is dipped into the liquid sample. In some embodiments, the solid support is first soaked in the culture media in the tube before sampling. In some embodiments, the solid support is dry before sampling. In some embodiments, the liquid sample is first cultured for a period of time ("culture enrichment"), for example, less than 24 hours, less than 12 hours, less than an enrichment period of 9 hours or less, 8 hours or less, 7 hours or less, 6 hours or less, 5 hours or less, 4 hours or less, 3 hours or less, or 2 hours or less.

In other embodiments, the sample may be enriched following capture of the microorganisms on the solid support. In some embodiments, the solid support with microorganisms can be incubated in growth media in the third compartment of the apparatus to allow the microorganism to expand in number. This step is referred to as incubation enrichment. In such embodiments, the enrichment period can be 1, 2, 3, 4, 5, 6, 7, or up to 8 hours or longer, depending on the sample type and size.

In some embodiments of the methods of the invention, the microorganisms may be detected without any isolation or purification of the microorganisms from a sample. For example, in certain embodiments, a sample containing one or more microorganisms of interest may be applied directly to the solid support and the assay is conducted in the apparatus.

Infection

The methods disclosed herein comprises operating the apparatus to cause the recombinant bacteriophage to contact the microorganisms of interest. Upon contacting the microorganisms, the bacteriophage replicate and express the indicator gene or reporter gene. See the section entitled "Recombinant Bacteriophage". The infection time, i.e., a time period between the time point when the sample is first contacted with bacteriophage and the time point when the substrate is added to the mixture, may vary, depending on the type of bacteriophage and concentration of the microorganisms in the sample. Using the apparatus in which the bacteria are captured on solid support can significantly reduce the time required for infection, for example, the infection time can be one hour or less, while in a standard assay, where no solid support is used to capture the bacteria, the infection is typically at least 4 hours, In certain embodiments, the time of infection for the methods disclosed herein is less than 6.0 hours, 5.0 hours, 4.0 hours, 3.0 hours, 2.5 hours, 2.0 hours, 1.5 hours, 1.0 hour, 45 minutes, or less than 30 minutes. In some embodiments, the time of infection is about 1 hour, about 2 hours, or about 3 hours.

Developing Signal

The indicator, produced by expression of the indicator gene, can be detected using methods well known to one or ordinary skill in the art. For example, one or more signal producing components can be reacted with the indicator to generate a detectable signal. In some embodiments, the indicator can be a bioluminescent compound. If the indicator is an enzyme, then amplification of the detectable signal is obtained by reacting the enzyme with one or more substrates or additional enzymes and substrates to produce a detectable reaction product. In an alternative signal producing system, the indicator can be a fluorescent compound where no enzymatic manipulation of the indicator is required to produce the detectable signal. Fluorescent molecules including, for example, fluorescein and rhodamine and their derivatives and analogs are suitable for use as indicators in such a system. In yet another alternative embodiment, the indicator moiety can be a cofactor, then amplification of the detectable signal is obtained by reacting the cofactor with the enzyme and one or more substrates or additional enzymes and substrates to produces a detectable reaction product. In some embodiments, the detectable signal is colorimetric. It is noted that the selection of a particular indicator is not critical to the present invention, but the indicator will be capable of generating a detectable signal either by itself, or be instrumentally detectable, or be detectable in conjunction with one or more additional signal producing components, such as an enzyme/substrate signal producing system.

In some embodiments, the detecting step will require addition of a substrate for the indicator enzyme to act on. Substrate can be added in a variety of ways. In some embodiments, the substrate is comprised in the second compartment of the apparatus and breaking the snap action seal causes the phage (in the first compartment in the apparatus) and substrate to contact the microorganisms (captured on the solid support) concurrently. See FIG. 12. In some embodiments, the snap action seals are broken sequentially, causing the microorganisms to contact the bacteriophage before contacting the substrate. See FIGS. 13A and 13B. In some embodiments, the method comprises operating the stop-lock to enable phased mixing such that the microorganisms contact bacteriophage before contacting the substrate.

In some embodiments, the reaction of indicator (e.g., luciferase) with substrate may continue for 30 minutes or more, and detection at various time points may be desirable for optimizing sensitivity. In some embodiments, luminometer readings may be taken initially and at 3-, or 5-, or 10-, or 15-minute intervals until the reaction is completed.

Detecting Signal

Detecting the signal produced by the indicator may include detecting emission of light. In some embodiments the compartment of the apparatus in which the substrate is mixed with the test sample is transparent, such that any signal resulting from the infection and subsequent incubation with substrate is visible. In this case, the signal can be detected through the wall of the compartment. In some embodiments, the apparatus containing the reacted sample is inserted into an instrument for detecting the signal that results. In other embodiments, a detecting instrument is used to scan the apparatus containing the reacted sample.

In some embodiments, a luminometer may be used to detect the indicator (e.g., luciferase), e.g., GloMax® 20/20 and GloMax® from Promega (Madison, WI). In some embodiments, a spectrophotometer, CCD camera, or CMOS camera may be used to detect color changes and other light emissions. Absolute RLU are important for detection, but the signal to background ratio also needs to be high (e.g., >2.0, >2.5, or >3.0) in order for single cells or low numbers of cells to be detected reliably. The background signal can be obtained by measuring control sample that does not contain microorganism using the same procedure as described above. In some embodiments, detection of signal from the reporter or indicator gene may include, for example, use of an instrument that employs photodiode or PMT (photomultiplier tube) technology. In some embodiments, a handheld luminometer may be employed for detection of signal.

Suitable PMT handheld luminometers are available from 3M (Maplewood, MN), BioControl (Seattle, WA), and Charm Science (Lawrence, MA). Suitable photodiode handheld luminometers are available from Hygiena (Camarillo, CA) and Neogen (Lansing, MI). These handheld luminometers typically produce much lower readings as compared to traditional luminometers (GloMax or GloMax 20/20) for the same sample. As shown in the Examples, multiple experiments show that the signals produced by the reactions were sufficient to be detected by these handheld luminometers. The assays were repeated multiple times with different types of microorganisms, including *L. monocytogenes* and *Salmonella*, and similar results were obtained each time. This indicates that the detection method using the apparatus is sufficiently sensitive and robust. Being able to use these handheld devices to detect the microorganism also offers convenience and flexibility that is often lacking with detection methods using traditional, non-handheld detection devices.

Systems and Kits of the Invention

In some embodiments, the invention comprises systems (e.g., automated systems) or kits comprising components for performing the methods disclosed herein. In some embodiments, the apparatus is comprised in systems or kits according to the invention. Methods described herein may also utilize such systems or kits. Some embodiments described herein are particularly suitable for automation and/or kits, given the minimal amount of reagents and materials required to perform the methods. In certain embodiments, each of the components of a kit may comprise a self-contained unit that is deliverable from a first site to a second site.

In some embodiments, the invention comprises systems or kits for rapid detection of a microorganism of interest in a sample. The systems or kits may in certain embodiments comprise: an apparatus as described above, and a signal detecting component, wherein the signal detecting component can detect the indicator gene product produced from infecting the sample with the recombinant bacteriophage. In some embodiments, the signal detecting component is a handheld device. In some embodiments, the signal detecting component is a handheld luminometer.

Thus in certain embodiments, the invention may comprise a system or kit for rapid detection of a microorganism of interest in a sample, wherein the system or kit comprises an apparatus comprising a first compartment comprising recombinant bacteriophage having a genetic construct inserted into a bacteriophage genome, wherein the construct comprises a promoter and an indicator gene. The system or kit may further comprise a second compartment that contain substrate, and/or a third compartment that contain media. One or more of these compartments are sealed and separate from the other portion of the apparatus by a snap-action seal, and the breaking the snap-action seal causes the contents from the compartment to leave the compartment and mix with the sample.

In some embodiments, the system may comprise a component for isolating the microorganism of interest from the other components in the sample.

In some systems and/or kits, the same component may be used for multiple steps. In some systems and/or kits, the steps are automated or controlled by the user via computer input and/or wherein a liquid-handling robot performs at least one step. In a computerized system, the system may be fully automated, semi-automated, or directed by the user through a computer (or some combination thereof).

These systems and kits of the invention include various components. As used herein, the term "component" is broadly defined and includes any suitable apparatus or collections of apparatuses suitable for carrying out the recited method. The components need not be integrally connected or situated with respect to each other in any particular way. The invention includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

In certain embodiments, the invention may comprise a system. The system may include at least some of the compositions of the invention. Also, the system may comprise at least some of the components for performing the method. In certain embodiments, the system is formulated as a kit. Thus, in certain embodiments, the invention may comprise a system for rapid detection of a microorganism of interest in a sample. The system may include at least some of the compositions of the invention. Also, the system may comprise at least some of the components for performing the method. In certain embodiments, the system is formulated as a kit. Thus, in certain embodiments, the invention may comprise a system for rapid detection of a microorganism of interest in a sample, comprising an apparatus as described above. For example, the apparatus may comprise a first compartment comprising recombinant bacteriophage having a genetic construct inserted into a bacteriophage genome, wherein the construct comprises a promoter and an indicator gene; wherein the solid support comprises a cell binding component. In some embodiments, the system also comprises a handheld detection device.

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD or Blu-Ray drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface. Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

EXAMPLES

The following examples describe detection of a low number of cells, even a single bacterium, in a shortened time to results and are to illustrate but not limit the invention.

Example 1. Detection of Microorganism of Interest in Bacterial Culture

This example demonstrates performance of the detection method using the apparatus with successful detection of bacteria present in a bacterial culture.

Assembling the Apparatus

100 µL A511/P100 Phage cocktail ($1.2 \times 10^9$ Pfu/mL) and 100 µL BHI media+1 mM $CaCl_2$ were added into top bulb of the apparatus (first compartment). A511/p100 phage is a phage that targets *Listeria moncytogenes*. A solid support press was used to press top components of the apparatus together. The apparatus tube was filled with 900 µL BHI media+1 mM $CaCl_2$. The solid support was then placed in the apparatus tube to absorb some media. The assembled apparatus (containing solid support soaked in media) were then kept overnight at 4° C.

Growing the Bacteria Culture

*Listeria moncytogenes* were grown overnight in BHI media (Becton Dickinson, Sparks, MD, USA in a shaking incubator. The overnight culture was then subcultured in BHI media to log phase at 37° C. Log phase cells were then diluted to appropriate number of cells (see FIG. 2). The solid support was removed from the apparatus and diluted cultures were spiked onto the solid support at the indicated CFU levels The solid support that were spiked with bacteria or media alone (control) were placed back into the apparatus tube and the tube was gently shaken to mix the content. (FIG. 2, Table 1)

In a similar experimental, 2 solid support was spiked with 10 CFU each of the bacteria. An uninoculated sample was used as a control. These samples were incubated overnight at 35° C. to expand the bacteria number before infection and substrate exposure (FIG. 2, Table 2)

Infection

The Snap-Valve was then broken by holding solid support firmly and breaking valve with thumb and forefinger. The phage (200 μL of 6×10[8] Pfu/mL) was expelled down by squeezing the bulb on the top of solid support tube. The contents in the solid support tube was gently mixed by swirling. The solid support was then placed in 30° C. incubator for 4 hours for phage infection of the bacteria. The NanoGlo substrate (Promega, Madison, WI) was diluted 1:4 with 70% ethanol and 10 μL diluted substrate was added into solid support tube. The content of the apparatus tube was mixed by vortexing and then let sit for 3 minutes.

Detection

Three detection methods were used. The solid support tube was inserted into Hygiena Handheld Luminometer. 1 mL of the infection mixture was removed and transferred to 1.5 mL microfuge tube to read on GloMax 20/20 Luminom-eter ("GloMax 20/20"), and 150 μl of the infection mixture was transferred to 96-well plate to be read on GloMax Luminometer ("GloMax"), The detection was then performed with solid supports that have been soaked in media overnight, with an infection time of 2 hours. The results are shown in FIG. 2, Tables 1 and 2. and the graphic representations of the results are shown in FIGS. 3A and 3B. The results show that with no growth enrichment (no overnight culturing of the sample before capturing with the solid support), the test is sensitive enough to detect 25,000 CFU on a Hygiena Handheld luminometer (FIG. 3A)—the readings for bacteria inoculated samples were all above the detection threshold of 10 relative lumi-nescence unit (RLU) criteria for positive samples and detect approximately 5,000 CFU on a GloMax 20/20 or a GloMax (FIG. 3B).

Example 2. Detection of *Salmonella* in Turkey Sample

Assemble the Apparatus

The apparatus was assembled as described in Example 1, except that the top bulb was filled with 100 μL SEA1/TSP1 Phage cocktail (1.2×10[7] Pfu/mL) and 100 μL TSB Media (ThermoFisher Oxoid, Grand Island, NY USA) and the apparatus tube was filled with 1 mL TSB media. SEA1/TSP1 phage is a phage that targets *Salmonella*.

Bacterial Inoculation of Ground Turkey

*Salmonella* culture was grown overnight and diluted for high and low CFU samples as described below 25 g test portions of ground turkey were divided into three groups: uninoculated group (5 samples,), high inoculated group (5 samples), and low inoculated group (20 samples). Each 25 g sample of the high group was inoculated with 2-10 CFU of *Salmonella*, and each sample of the low group was inoculated with 0.2-2 CFU of *Salmonella*. Samples were then placed in filtered sample bags and stored at 4° C. for 48-72 hours.

Enrichment of Bacteria in Inoculated Ground Turkey

Pre-warmed TSB media (41° C.) was added to each sample at a sample to medium ratio of 1:3. The sample was then blended on STOMACHER® for 30 seconds on high, and then incubated at 41° C. without shaking for 24 hours to enrich the bacteria in the sample.

Sampling

The test sample was obtained by dipping the solid support into each enriched sample and swirling around for 10 seconds to absorb maximum amount of sample. The solid support was placed into the apparatus tube filled with TSB media. The tube was gently shaken to mix the contents in the tube, and then either immediately infected or placed in 37° C. for an additional hour before infection.

Infection

The Snap-Valve of the compartment housing the bacte-riophage was then broken by holding solid support firmly and breaking valve with thumb and forefinger. The phage (200 μL of 6×10[6] Pfu/mL) was expelled down into the tube by squeezing the bulb on the top of apparatus tube. The contents in the apparatus tube was gently mixed by swirling. The solid support was then placed in 37° C. incubator for 30 min or 2 hours for phage infection of the bacteria. The NanoGlo substrate (Promega, Madison, WI) was diluted 1:4 with 70% ethanol and 10 μL diluted substrate was added into the apparatus tube. The content of the apparatus tube was mixed by vortexing and then let sit for 3 minutes. The signals were detected as described in Example 1. The results from uninoculated samples (control group) are shown in FIG. 4, Table 3 and inoculated samples (experimental group) are shown in Table 4. The graphic representation of the results are show in FIG. 5A and FIG. 5B.

The results show that each of the three detection devices used were able to detect all turkey samples that were positive for *Salmonella* after a 24 hour culture enrichment. Signal from GloMax and GloMax 20/20 were much higher than Hygiena Luminometer. Incubation time (i.e., incubation of the solid support that has captured the bacteria with the media before infection) and infection time are factors that may affect the signal intensity. Of the various additional incubation times and infection times tested, 0 hour incuba-tion time and 2 hour infection time resulted in the highest RLUs followed by samples that have 1 hour incubation time and 0.5 hour infection time, and then by samples that have 0 hour incubation time and 0.5 hour infection time. The results also show that 0 hour incubation and 2 hour infection has the lowest background signal.

Example 3. Additional Studies for Testing Effect of Infection Time on Sensitivity of the Assay The experiment was set up as described in Example 2, except that after the solid support was dipped into the bacterial turkey sample, the solid support was placed in media and infection is performed immediately, i.e., no incubation time for the bacteria on the solid support to grow. The infection time varied from 30 min to 2 hour. The signals were detected as described above. The results of three samples are shown in FIG. 6 and the data are plotted in FIG. 7A-7C. The results show that infection of 2 hours can increase signal as indicated in samples 24 and 26 did not show signal in Hygiena at 30 min but did for 2 hour infection.

FIG. 8A-8C shows comparison between the GloMax and the GloMax 20/20 different devices. GloMax and GloMax 20/20 showed similar results.

Example 4. Testing *L. monocytogenes* 19115 Environmental Sponge Samples

*L. monocytogenes* were inoculated onto ceramic tiles surfaces and allowed to dry and sit at room temperature for 18-24 hours. Sample sponges were used to swab the ceramic tiles and sponges were placed into a bag for enrichment for 24 hours at 35° C. The solid support was then used to sample the enriched samples as described in Example 2. 100 μL

*Listeria* phages (at a concentration of 1.2×10⁸ PFU/ml) were used to infect the bacterial turkey culture for one hour at 30° C. The signals were detected using GloMax and Hygiena. The results are shown in FIG. 9. The results show that Hygiena handheld can detect *L. moncytogenes*-contaminated environmental sample.

Example 5. Different Detection Devices

Experiments were set up as described in Example 2. The phage infection time was 1 hour at 37° C. The signals were read on GloMax, a 3M handheld luminometer ("3M"), and Hygiena the results are shown in FIG. 10. It shows that 3M is more sensitive in detecting signals.

We claim:

1. A device comprising:
a first compartment immediately adjacent to a second compartment wherein:
the first compartment comprises (i) a recombinant bacteriophage having a genetic construct inserted into the bacteriophage genome, wherein the genetic construct comprises a viral promotor and an indicator gene, and (ii) an inlet/portal for adding a sample comprising one or more microorganisms of interest to the first compartment, wherein the inlet/portal comprises a first seal configured such that the sample is added to the recombinant bacteriophage by breaking the first seal; and
a second compartment comprising a signal detecting component, wherein the second compartment is separated from the first compartment by a second seal, wherein upon breaking the second seal, the signal detecting component facilitates detection of an indicator gene product produced as a result of infecting the one or more microorganisms of interest in the sample with the recombinant bacteriophage after the addition of the sample to the first compartment;
wherein the device is free of media.

2. The device of claim 1, wherein the signal detecting component is a substrate and the indicator gene encodes an enzyme.

3. The device of claim 2, wherein the enzyme is a luciferase.

4. A method to detect one or more microorganisms of interest in a sample comprising the steps of:
contacting the sample with an infectious reagent in a device comprising a first and a second compartment, wherein the one or more microorganisms of interest in the sample, if present, are infected by the infectious agent,
wherein the device is free of media and the first compartment comprises (i) the infectious agent, wherein the infectious agent is a recombinant bacteriophage having a genetic construct inserted into a bacteriophage genome, wherein the construct comprises a viral promoter and an indicator gene, and (ii) an inlet/portal for adding the sample, wherein the inlet/portal comprises a first seal;
contacting the recombinant bacteriophage from the first compartment with the sample by adding the sample to the first compartment by breaking the first seal such that the recombinant bacteriophage infects the one or more microorganisms of interest in the sample, thereby producing an indicator gene product, and
detecting the indicator gene product in the second compartment wherein the second compartment comprises a substrate, wherein the second compartment is immediately adjacent to the first compartment and is separated from the first compartment by a second seal, wherein detecting the indicator gene product comprises breaking the second seal to contact the substrate with the indicator gene product.

5. The method of claim 4, wherein the method further comprises binding microorganisms in the sample to a solid support.

6. The method of claim 5, wherein the solid support is a bead.

7. The method of claim 5, wherein the solid support comprises polyethylene (PE), polypropylene (PP), polystyrene (PS), polylactic acid (PLA) and polyvinyl chloride (PVC).

8. The method of claim 4, wherein the bacteriophage is lyophilized.

9. The method of claim 4, wherein the bacteriophage is in contact with the sample for 0.2-3 hours before detecting the indicator gene product.

10. The method of claim 4, wherein the indicator gene product comprises at least one of a fluorophore, a fluorescent protein, a particle, and an enzyme.

11. The method of claim 10, wherein the enzyme comprises at least one of a luciferase, a phosphatase, a peroxidase, and a glycosidase.

12. The method of claim 11, wherein the luciferase is a genetically engineered luciferase.

13. The method of claim 4, wherein the sample is a food, environmental, water, commercial, or clinical sample.

14. The method of claim 4, wherein the method detects as few as 10, 9, 8, 7, 6, 5, 4, 3, 2, or a single bacterium in a sample of a standard size for the food safety industry.

15. The method of claim 4, wherein the sample comprises meat or vegetables.

16. The method of claim 4, wherein the sample is a food, water, dairy, environmental, commercial, or clinical sample.

17. The method of claim 4, wherein the sample is first incubated in conditions favoring growth for an enrichment period of 9 hours or less, 8 hours or less, 7 hours or less, 6 hours or less, 5 hours or less, 4 hours or less, 3 hours or less, or 2 hours or less.

* * * * *